US012276655B2

(12) United States Patent
Svahn et al.

(10) Patent No.: US 12,276,655 B2
(45) Date of Patent: Apr. 15, 2025

(54) MSC PREDICTION ALGORITHM

(71) Applicant: NEXTCELL PHARMA AB, Huddinge (SE)

(72) Inventors: Mathias Gosta Svahn, Nacka (SE); Johanna Dahllund, Tullinge (SE); Bahareh Khalaj, Sundbyberg (SE)

(73) Assignee: NEXTCELL PHARMA AB, Huddinge (SE)

( * ) Notice: Subject to any disclaimer, the term of this patent is extended or adjusted under 35 U.S.C. 154(b) by 1050 days.

(21) Appl. No.: 17/256,910

(22) PCT Filed: Jul. 2, 2019

(86) PCT No.: PCT/SE2019/050657
§ 371 (c)(1),
(2) Date: Dec. 29, 2020

(87) PCT Pub. No.: WO2020/009648
PCT Pub. Date: Jan. 9, 2020

(65) Prior Publication Data
US 2021/0372992 A1    Dec. 2, 2021

(30) Foreign Application Priority Data
Jul. 2, 2018    (SE) ..................... 1850829

(51) Int. Cl.
*G01N 33/50* (2006.01)
*G01N 33/68* (2006.01)
(52) U.S. Cl.
CPC ..... *G01N 33/5047* (2013.01); *G01N 33/5073* (2013.01); *G01N 33/6854* (2013.01); *G01N 2333/90241* (2013.01); *G01N 2800/52* (2013.01)
(58) Field of Classification Search
None
See application file for complete search history.

(56) References Cited

U.S. PATENT DOCUMENTS

| 2003/0190665 | A1 | 10/2003 | Vandenbark |
| 2011/0038881 | A1 | 2/2011 | Ball |

FOREIGN PATENT DOCUMENTS

| EP | 2982746 | 2/2016 |
| WO | 2015016761 | 2/2015 |
| WO | 2016170187 | 10/2016 |

OTHER PUBLICATIONS

Coulson-Thomas et al. "Extrinsic and Intrinsic Mechanisms by Which Mesenchymal Stem Cells Suppress the Immune System" 2016, Laboratory Science, vol. 14, No. 2: 121-134. (Year: 2016).*

The International Search Report (ISR) for PCT/SE20191050657, dated Sep. 17, 2019, pp. 1-8.
Written Opinion of the International Searching Authority for PCT/SE2019/050657, dated Sep. 17, 2019, pp. 1-11.
Dominici, et al. (2006). Cytotherapy 8: 315-317.
Berman et al, (2010) Diabetes 59: 2558-2558.
Madsbad et al.,(1979) Br Med J; 2(6200): 1257-9.
Steffes et al., (2003) Diabetes Care; 26(3): 832-6.
Chen and Hou, (2016) Stem Cell Res Ther. 7: 16.
Vercelli, et al. 2008; Neurobiol Dis. Sep. 2008;31(3):395-405.
Mazzini, et al., 2003; ALS Other MN Disord. Sep. 2003;4(3):158-61.
Forostyak, et al. 2011 Cytotherapy. Oct. 2011; 13(9): 1036-46.
Rasmusson et al., (2005) Exp.Cell.Res, 305 (1) (2005), pp. 33-41.
Rustenhoven et al., Scientific Reports (2016) Sci Rep; 19371.
Von Bahr et al., (2012) Biol Blood Marrow Transplant; 18: 557-564.
Von Bahr L et al., (2012). Stem Cells; 30: 1575-1578.
Hu J et al., (2013). Endocr J; 60: 347-357.
Carlsson PO et al., (2015) Diabetes. 2015; 64(2):587-92.
Zafranskaya MM et al Immunol Lett, 2013, vol. 149, pp. 9-18.
Zafranskaya M. et Scand J Immunol, 2013, vol. 78, pp. 455-462.
Mulder A. et al Clin Exp Immunol, 2001, vol. 124, pp. 9-15.
Shi Y. et al Nat Rev, Jun. 12, 2018, vol. 14, 493-507.
Dugast A-S. et al J Immunol, 2017, vol. 180, pp. 7898-7906.
Diane Carter, Alicia Tyrell, Simon Bubnic, Michelle Marcelino, Keren Kedzierski, Rod Monroy, Randy Mills, Alla Danilkovitch. Prochymal Product Development. (Meeting Abstract #4322) "Characterization of MSC Potential to Treat GVHD Using Molecular Markers Linked to MSC-Mediated Immunosuppression In Vitro." Osiris Therapeutics, Inc. Baltimore, MD, USA.
Peter J. Cowan and Anthoiny J.F. d'Apice, "Xenoimmunity", Chapter 12, Textbook of Organ Transplantation. First Edition. edited by Allan D. Kirk et al. 2014 John Wiley & Sons.
Ma Z, Kim Y, Hu F, Lee JK. Point success rate for patient therapeutic response prediction by continuous biomarker scores. Stat Methods Med Res. Aug. 2016;25(4):1638-47. doi: 10.1177/0962280213493161. Epub Jul. 9, 2013. PMID: 23839122; PMCID: PMC7771551.
Lohan P, Treacy O, Griffin MD, Ritter T, Ryan AE. Anti-Donor Immune Responses Elicited by Allogeneic Mesenchymal Stem Cells and Their Extracellular Vesicles: Are We Still Learning? Front Immunol. Nov. 24, 2017;8:1626. doi: 10.3389/fimmu.2017.01626. PMID: 29225601; PMCID: PMC5705547.
Chinnadurai R, Rajan D, Qayed M, Arafat D, Garcia M, Liu Y, Kugathasan S, Anderson LJ, Gibson G, Galipeau J. Potency Analysis of Mesenchymal Stromal Cells Using a Combinatorial Assay Matrix Approach. Cell Rep. Feb. 27, 2018;22(9):2504-2517. doi: 10.1016/j.celrep.2018.02.013. PMID: 29490284; PMCID: PMC5855117.

(Continued)

Primary Examiner — Teresa E Knight
(74) Attorney, Agent, or Firm — McDonnell Boehnen Hulbert & Berghoff LLP

(57) ABSTRACT

The present invention relates to a method of in vitroprediction of the in vivoefficacy in a patient of treatment with a drug product based on an overall assessment of the properties patients own immune cells when exposed to the drug product with and/0 or without stimulation; the drug product when exposed to said patients own immune cells; and any preexisting antibodies against said drug product in said patient.

17 Claims, 1 Drawing Sheet

(56) References Cited

OTHER PUBLICATIONS

Davies LC, Alm JJ, Heldring N, Moll G, Gavin C, Batsis I, Qian H, Sigvardsson M, Nilsson B, Kyllonen LE, Salmela KT, Carlsson PO, Korsgren O, Le Blanc K. Type 1 Diabetes Mellitus Donor Mesenchymal Stromal Cells Exhibit Comparable Potency to Healthy Controls In Vitro. Stem Cells Transl Med. Nov. 2016;5(11):1485-1495. doi: 10.5966/sctm.2015-0272. Epub Jul. 13, 2016. PMID: 27412884; PMCID: PMC5070499.

* cited by examiner

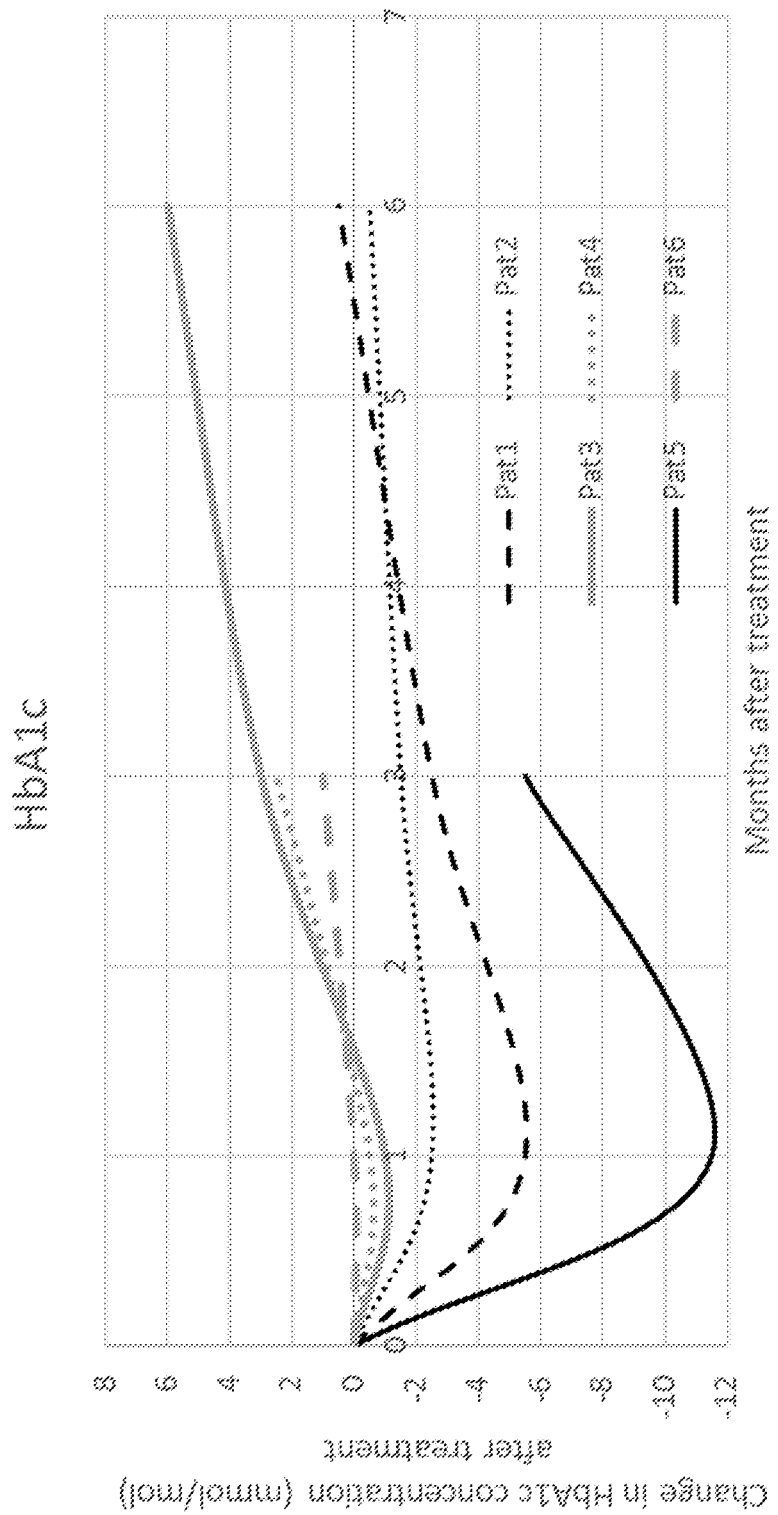

MSC PREDICTION ALGORITHM

CROSS REFERENCE TO RELATED APPLICATION

This application is a U.S. national phase of International Application No. PCT/SE2019/050657, filed Jul. 2, 2019, which claims priority to Swedish Patent Application No. 1850829-1, filed Jul. 2, 2018, both of which are incorporated by reference herein in their entirety.

TECHNICAL FIELD

The present invention relates to a method of in vitro prediction of the in vivo efficacy in a patient of treatment with a drug product based on an overall assessment of the properties of the drug product, said patient's immune cells, and/or presence of anti-HLA antibodies in said patient, wherein said assessment is based on at least two function and/or potency assays. The invention further relates to uses of said method for making personalized treatment decisions.

BACKGROUND

Cell therapy and therapies where the drug product is from a donor cell origin, are generally costly and the efficacy of the therapy may vary between patients. This is particular apparent in the field of immunomodulation and anti-inflammatory therapy where cells or cell products do not need HLA matching since no engraftment is anticipated. An off the-shelf drug product can be produced in large quantities and the cost of therapy can thus be greatly reduced.

Mesenchymal stem cells (MSCs) are non-hematopoietic cells expressing the surface markers CD73, CD90, and CD105 while lacking the expression of CD14, CD34, and CD45. When expanded as polyclonal cultures, they are a heterogenous population of cells with retained capacity for self-renewal and differentiation into various forms of mesenchyme (Dominici, et al. (2006). Cytotherapy 8: 315-317). In vitro, MSCs must be adherent to plastic under standard tissue culture conditions, and have the capacity to differentiate into osteocytes, adipocytes, and chondrocytes. MSCs can be found not only in bone marrow, in which they were originally found, but also in almost all other forms of tissues and here the term MSCs include MSCs from all tissues e.g. from CNS, tooth, adipose, liver, pancreas, blood, lymph, urine, Wharton's jelly, placenta and amniotic fluid.

MSCs have the capacity to promote survival, angiogenesis, tissue repair and modulate responses by innate and adaptive immune cells (Berman et al, (2010) Diabetes 59: 2558-2568). Thus, transplantation of MSCs present an attractive therapeutic option for example in the field of autoimmune disease, inflammatory disease and transplant rejection.

An example of autoimmune diseases is autoimmune diabetes (also known as type 1 diabetes, T1D, latent autoimmune diabetes in the adult, LADA) which is a form of diabetes in which not enough insulin is produced. The underlying mechanism involves an autoimmune destruction of the insulin-producing beta cells in the pancreas. At clinical onset of T1D the beta-cell mass may have decreased to 15-40% of normal levels. Maintenance of residual insulin secretion is important in contributing to lower HbA1c, fewer blood glucose fluctuations, and diminished risk of ketoacidosis (Madsbad et al., (1979) Br Med J; 2(6200): 1257-9; Steffes et al., (2003) Diabetes Care; 26(3): 832-6). It also substantially decreases the risks of severe hypoglycemic events and late complications. An identified successful intervention may not only be used to delay and prevent disease but also be applied to patients with ongoing disease before overt hyperglycemia, thereby providing means to prevent further disease development.

Renal transplant (also known as kidney transplant) is the most common kind of solid organ transplantation with 19,850 transplantations during 2017, constituting 57% of all organ transplants, according to United Network for Organ Sharing. Organ transplant is a last resort for patients with end-stage renal disease and the medical need of a transplant exceeds the number of available organs by far. Kidneys are donated by living donors (usually a relative with two fully functional kidneys) or by a deceased-donor (formerly known as cadaveric donor). Side effects of current immunosuppressive drugs, such as nephrotoxicity, opportunistic infection, and tumorigenic potential, influence long-term graft outcomes. In recent years, continued research and subsequent discoveries concerning the properties and potential utilization of mesenchymal stromal/stem cells (MSCs) have aroused considerable interest and expectations. However, many studies have shown that the biological activity of MSCs depends on internal inflammatory conditions (Chen and Hou, (2016) Stem Cell Res Ther. 7: 16).

The cellular and molecular features of MSCs makes them an encouraging candidate to treat amyotrophic lateral sclerosis (ALS). MSCs can support motor neurons and surrounding cells, reduce inflammation stimulate tissue regeneration and release growth factors. It has been shown that intravenous, intrathecal, intracerebral and intraspinal administration of MSC into SOD1 G93A mouse model led to advanced motor function, decrease in the inflammatory response, decreased loss of motor neurons and long time-time survival (Vercelli, et al. 2008; Neurobiol Dis. 2008 September; 31(3):395-405. Mazzini, et al., 2003; ALS Other MN Disord. 2003 September; 4(3):158-61. Forostyak, et al. 2011; Cytotherapy. 2011 October; 13(9):1036-46).

Cell therapy and cell products such as exosomes are attractive drug product for advanced therapies since HLA matching is of low or no importance. Therapies are generally well tolerated but there is a need in the field to improve and predict the treatment outcomes for patient's suffering from autoimmune disease, such as autoimmune diabetes, ALS, and patient's receiving organ transplants.

SUMMARY OF THE INVENTION

An object of the present invention is to provide a methods for in vitro prediction of the in vivo efficacy of a treatment with a specific drug product for a specific patient, in other words personalized treatment efficacy prediction. Also, an object of the invention is to provide methods of treatment wherein said prediction is used to make personalized treatment decisions for said patient and related in vitro uses of said drug products and related systems. As different patients may respond differently to treatment with drug products it is of importance to be able predict the treatment outcome for each individual patient or patient group. It is an object to overcome the drawbacks of the prior art. It is envisioned that the method for in vitro prediction and related aspects as described herein achieve the present objects.

Thus, in a first aspect of the present invention, there is provided a method for in vitro prediction of the in vivo efficacy in a patient of treatment with a drug product based on an overall assessment, said method comprising the step of evaluating at least properties a) and b) or at least properties b) and c) by at least 2 assays, wherein said properties are:
- a) The in vitro reaction of said patient's own immune cells when exposed to the drug product, for example with and/or without stimuli;
- b) The reaction of said drug product when exposed to said patient's own immune cells; and
- c) Any preexisting antibodies in said patient, which antibodies exhibit affinity for said drug product.

In particular, the inventive method as disclosed herein evaluates and predicts the not only how the patient reacts to the drug product (for example how the patient's own immune cell react to said drug product or the presence of preexisting antibodies with specificity to said drug product in said patient, which presence could lead to adverse side effects of treatment), but also how the drug product reacts to the patient. This is of particular importance as the drug product as disclosed herein comprises biologically active material, for example but not limited to cells, which may react to the biological environment of the patient. Thus, the present method evaluated the interplay of the patient and the drug product in order to predict in vivo efficacy of said drug product.

In one embodiment, there is provided a method as disclosed herein, wherein said step of evaluating at least said properties a) and b) or at least said properties b) and c) comprises evaluating all three properties a), b) and c).

In some embodiments, it may be beneficial that said drug product and/or the patient's own immune cells assayed with at least one or more functional and/or potency assays in order to obtain more information about the properties drug product and the predicted response of patient's own immune cells to said product.

Thus, in one embodiment there is provided a method for in vitro prediction as disclosed herein, wherein said at least two assays are functional and/or potency assays. It will be understood that said at least two assays may be one assay evaluating property a) and one assay evaluating property b) or one assay evaluating property b) and one assay evaluating property c). If more assays are employed, several assays may be used to evaluate any one of properties a), b) and c). For example, said at least two assays may be least 3, 4, 5, 6, 7, 8 or more assays. It may be beneficial that said assays are at least one functional assay, such as at least two functional assays, such as at least three functional assays, such at least four functional assays, such least five functional assays; and at least one potency assay, such as at least 2 potency assays. It will be appreciated that each of properties a) and b), may be evaluated by several assays, which may or may not be the same. It will also be appreciated that if more assays are employed, the accuracy of prediction may be improved in some embodiments of said method.

As used herein, the term "potency" refers to a cell's ability to differentiate into other cell types. The more cell types a cell can differentiate into, the greater its potency. It will be appreciated that the potency of the drug product may be evaluated. As used herein, the term "potency assay" refers to an assay which may be used for evaluating the potency the drug product.

As used herein, the term "functional assay" refers to an assay which evaluates a property of interest of said drug product, for example the effect of the drug, product on the patient's cells or the effect of said cells on the drug product. The skilled person will appreciate that said assays may be tailored to reflect the properties which are desired in the drug product. For example, in the case wherein it is desired that the product has immunosuppressive properties, the assays may be selected to reflect this property of interest. It will be appreciated that the predictive method as disclosed herein is envisioned to be applicable or adaptable to any inflammatory state of a patient in need of treatment.

As used herein, the term "drug product" refers to the potentially therapeutic product to be evaluated. To clarify, the drug product may be comprised in a composition, such as a therapeutic composition, such as a composition for cell therapy. The skilled person will appreciate that said composition may further comprise physiologically and/or therapeutically acceptable excipients. For example, said drug product may be a cell composition for cell therapy; a composition comprising fractions of cells; organelles; vesicles; exosomes; a protein drug or composition; a nucleic acid based drug or composition; or small molecule drug or composition. The skilled person will appreciate that said cell composition for cell therapy, composition comprising fractions of cell, organelle, vesicles and/or exosomes as described in the present disclosure comprises cells or fractions thereof, organelles, vesicles and/or exosomes isolated from their natural environment. Thus, in the context of the present disclosure, when the drug product is disclosed to comprise cells, fractions thereof, organelles, vesicles or exosomes or to be cells, fractions thereof, organelles, vesicles or exosomes it is to be understood to mean that the drug product comprises or is cells, fractions thereof, organelles, vesicles or exosomes isolated from their natural environment, in other words isolated cells. This may be indicated by the wording "isolated", but in some instances the wording "isolated" is not used. The skilled person will appreciate that it is to be understood that the cells, fractions thereof, organelles, vesicles or exosomes disclosed herein are nevertheless isolated from their natural environment.

In particular, said drug product may be isolated live cells or a live cell composition for cell therapy, such as transplantation of cells; isolated non-live cells or a non-live cell composition for cell therapy (for example dead or lyophilized cells), such as transplantation of cells; an isolated non-whole cell composition, such as a compositions comprising fractions of cell; an isolated composition comprising extra cellular vesicle obtained from cell culture media; or an isolated composition comprising exosomes. In a particular embodiment, said drug product comprises an isolated cell composition, for example a cell population, such as a live cell population, such as a live mesenchymal stromal/stem cells (MSCs) population. In a particular embodiment, said drug product is a cell composition, for example a cell population, such as a live cell population, such as a live MSC population. In one embodiment, said drug product comprises live cells, such as live MSCs.

Thus in one embodiment, said drug product comprises whole cells, such as live cells, dead cells, or lyophilized cells; extracellular vesicles obtained from cell culture; exosomes; or conditioned media. In one particular embodiment, said cells are MSCs, such as such as live MSCs, dead MSCs, or lyophilized MSCs; extracellular vesicles obtained from MSCs cultures; or exosomes from MSCs. In one particular embodiment, said cells are live cells, such as live MSCs. In one embodiment, said cells are isolated live cells, such as isolated live MSCs. In one embodiment, said MSCs are an allogeneic MSC population, such as an isolated allogeneic MSC population, In particular, said cells may be a pooled allogeneic MSC population, such as an isolated pooled allogeneic MSC population.

In one embodiment of the method as disclosed herein said drug product is selected from the group consisting of MSCs, exosomes from MSCs and vesicles from MSCs.

As used herein, the terms "MSCs", "mesenchymal stem cells", "mesenchymal stromal cells" and "marrow stromal cells" refer to cells with the above mentioned properties. The present disclosure adheres to the definition of MSC according to the criteria of the International Society for Cellular Therapy (ISCT). MSCs can be derived from bone marrow, peripheral blood, adipose tissue, dental tissue, placenta, umbilical cord, amniotic fluid, cord blood, Wharton Jelly, decidua, chondrion membrane and amnion membrane.

Hence, the predictive method is envisioned to be applicable for evaluation of a treatment with any one of said MSCs, exosomes or extracellular vesicles, with any other cell therapy composition, in particular any composition suitable for the treatment and/or prevention of an inflammatory condition, an autoimmune disease or transplant rejection. Thus, the predictive method as disclosed herein is envisioned to be applicable for evaluation of a treatment option for a group of patients or for an individual patient.

Transplanted MSCs are expected to be cleared within days and some scientists argue that the living cells are not actually needed. Without being bound by theory, it might be sufficient to use exosomes and extracellular vesicles for therapy. MSCs are known to have anti-inflammatory effect with low or no expression of HLA-dr but other naïve or genetically modified cell lines can also be used for production of exosomes and/or extracellular vesicles.

In one particular embodiment there is provided a method as disclosed herein, said MSCs are an allogeneic MSC population, such as a pooled allogeneic MSC population. In one embodiment, said pooled allogeneic MSC population comprises cells derived from at least 1, such as at least 2, such as at least 3, such as at least 4, such as at least 5, such as at least 6, such as at least 7, such as at least 8, such as at least 9, such as at least 10 individual donor(s). As used herein, the term "pooled" when referring to a MSC population refers to an MSC population comprising cells derived from at least 2 individual donors.

As used herein, the term "at least one" refers to one or more. Similarly, the term "at least two" refers to two or more, and so on.

The present inventors expect that an isolated, pooled allogeneic MSC population may exhibit low immunogenic properties. Thus in one embodiment there is provided a method for in vitro prediction as described herein, wherein said allogeneic MSC population is an isolated, pooled allogenic MSC population, such as a population wherein the number of cells derived from any one donor does not exceed 50% of the total cell number.

In one embodiment there is provided a method as disclosed herein, wherein said MSC in the pooled allogeneic MSC population have at most been subject to seven passages, such as at most six passages, such as at most five passages, such as at most four passages, such as at most three passages, such as one, two or three passages, such as two or three passages. It is to be appreciated that the number of passages is related to the number of cells present in the culture. Thus, it may be beneficial to retain a balance between cell number and maintained potency in order to obtain a sufficient number of cells with desirable properties. Thus, in some embodiments the said MSCs have been subject to 2-6, such as 2-5, such as 2-4, such as 2-3 passages.

As used herein, the term "passage" refers to transferring cells from a previous culture to fresh growth medium.

In one embodiment, there is provided a method as disclosed herein, wherein said MSCs are selected from the group consisting of bone marrow derived MSCs, peripheral blood derived MSCs, adipose tissue derived MSCs, dental tissue derived MSCs, placenta derived MSCs, umbilical cord derived MSCs, amniotic fluid derived MSC, cord blood derived MSCs, Wharton Jelly derived MSCs, decidua derived MSCs, chondrion membrane derived MSCs and amnion membrane derived MSCs. In particular embodiments, said MSCs are selected from the group consisting of placenta derived MSCs, umbilical cord derived MSCs, amniotic fluid derived MSC, cord blood derived MSCs, Wharton Jelly derived MSCs, decidua derived MSCs, chondrion membrane derived MSCs, dental pulp and amnion membrane derived MSCs; such as placenta derived MSCs, umbilical cord derived MSCs, amniotic fluid derived MSC, cord blood derived MSCs, Wharton Jelly derived MSCs, decidua derived MSCs, dental pulp derived MSCs and amnion membrane derived MSCs; such as placenta derived MSCs, umbilical cord derived MSCs, amniotic fluid derived MSC, cord blood derived MSCs, Wharton Jelly derived MSCs, dental pulp derived MSCs; such as placenta derived MSCs, umbilical cord derived MSCs, cord blood derived MSCs and Wharton Jelly derived MSCs; such as umbilical cord derived MSCs, cord blood derived MSC and Wharton Jelly derived MSCs. In one embodiment, said MSCs are umbilical cord derived MSCs or Wharton Jelly derived MSCs.

As used herein, the term "patient" refers to an animal, such as a mammal, such as a human.

As used herein the term "patient's own immune cells" refers to peripheral blood mononuclear cell (PBMC) in other words any peripheral blood cell having a round nucleus (which includes lymphocytes (T cells, B cells, NK cells) and monocytes; or microglia. Said cells may be taken from the patient's blood, lymph, lymph-node, CSF, urine, joint, tumor (if found), bone marrow, adipose. The patient's own immune cells may be activated and/or stimulated to enhance or mimic the inflamed state to be treated before analysis of response. Thus, in one embodiment there is provided a method for in vitro prediction as disclosed herein, wherein said patient's own immune cells are selected from the group consisting of peripheral blood monocyte cells (PBMC); T lymphocytes from peripheral blood; T lymphocytes from the central nervous system (CNS); and microglia cells from the CNS. In one embodiment, said patient's own cell are selected from the group consisting of PBMC and microglia.

The activated or stimulated patient's own immune cells are then later exposed to the drug product, and the drug product's potential to revert the inflamed state, is analyzed. Hence, the method for in vitro prediction as disclosed herein may employ at least 2 assays, such as least 3 assays, such as at least 4 assays, such as at least 5 assays, such as at least 6 assays or more for said analysis.

In one embodiment, said assays may comprise at least one assay measuring the immunosuppressive capacity of said drug product. For example, the immunosuppressive capacity of the drug product may be measured as an effect/outcome on the patient's own immune cells. The immunosuppressive capacity may also be measured for example by analyzing the expression of a biomarker in said drug product, which biomarker is indicative of the immunosuppressive effect of the drug product. Thus, said immunosuppressive capacity may be measured in property a) and/or b). As used herein, the term "immunosuppressive capacity" refers to the capacity to elicit a reduction of the activation or efficacy of the immune system. The skilled person will appreciate that the immunosuppressive capacity may be measured directly or indirectly in an assay.

In one embodiment there is provided a method for in vitro prediction as disclosed herein, wherein evaluation of property a) or b) comprises co-cultivation of the patient's own immune cells with the drug product.

In one embodiment, the evaluation of property a) comprises evaluation of protein expression of the patient's own immune cells when the patient's own immune cells are co-cultivated with the drug product. In one embodiment, said property a) is evaluated with or without stimuli.

In one particular embodiment said evaluation of protein expression in property a) is the evaluation of the expression at least one of the markers selected from the group consisting of CD11b, CD14, CD68 and CD200r, such as evaluation of the expression of at least of CD14. CD14 is a component of the innate immune system and is a co-receptor for detection of bacterial lipopolysaccharides; CD11b is an integrin family member and is expressed on the surface of many leukocytes including monocytes, neutrophils, natural killer cells, granulocytes and macrophages; CD68 is a glycoprotein which binds to low density lipoprotein and is expressed on monocytes/macrophages; CD200r is a cell surface transmembrane glycoprotein and is expressed on the surface of myeloid cells and CD4+ T cells. Thus, in one embodiment, a change in the expression of any one of markers selected from the group consisting of CD11b, CD14, CD68 and CD200r is indicative of favorable response of patient's own immune cells to said drug product. In one embodiment, an increase or decrease change in the expression of any one of markers selected from the group consisting of CD11b, CD14, CD68 and CD200r is indicative of favorable response of patient's own immune cells to said drug product. To clarify, a change in the expression of any one of markers selected from the group consisting of CD11b, CD14, CD68 and CD200r is indicative of change in proinflammatory or regenerative phenotype of the patient's own cells.

In another embodiment there is provided a method for in vitro prediction as disclosed herein, wherein evaluation of property b) comprises evaluation of protein expression of the drug product when the drug product is co-cultivated with patient's own immune cells.

In one embodiment of said method for in vitro prediction, for property b) said at least 2 functional and/or potency assays evaluate at least one of alterations in proliferation; protein expression; protein excretion; and cell marker expression. In one particular embodiment, said property b) is evaluated with or without stimuli. In one embodiment there is provided a method for in vitro prediction as disclosed herein, wherein said at least 2 assays comprise at least one assay measuring the immunosuppressive capacity of said drug product in property a) and/or b).

In one embodiment there is provided a method for in vitro prediction as disclosed herein, wherein said at least one assay measuring the immunosuppressive capacity of said drug product measures indoleamine-2,3-dioxygensase (IDO) activity in property b). An immunosuppressive potential may reported as a measure of IDO activity, determined by measuring tryptophan and kynurenine in the culture supernatant. IDO is a heme-containing enzyme that in humans is encoded by the IDO1 gene. The IDO enzyme converts L-tryptophan to N-formylkynurenine (or kynurenine), an immunosuppressive molecule that acts as an inhibitor of immune cell proliferation, including T cells. The IDO activity may be presented as the ratio of kynurenine/tryptophan and can be determined by calculating the amount of tryptophan and kynurenine present in cell culture supernatants for example using an ELISA kit. IDO activity may also be presented as plasma concentration of kynurenine. When stimulated with interferon gamma (IFNγ), mesenchymal stem/stroma cells (MSCs) secrete more IDO than when they are unstimulated.

Inducible IDO activity indicates that the cells have functional potency, related to immunomodulation and/or immunosuppression. In this context, an increased IDO activity is to be interpreted as that the drug product exhibits immunosuppressive capacity and thus may be suitable for treatment, such as an immunosuppressive treatment, of a patient in need thereof. It is to be understood that said IDO activity may be measured in the drug product is exposed to the patient's own immune cells.

In one embodiment there is provided a method for in vitro prediction as disclosed herein, wherein said at least one assay measuring the immunosuppressive capacity of said drug product measures the effect of said drug product on the proliferation of peripheral blood mononuclear cells (PBMCs), such as for example T-lymphocytes. In this context, said effect may be measured in property a) or b), in particular in property a). The proliferation of T-lymphocytes, such as proliferation of phytohemagglutinin (PHA) stimulated T-lymphocytes may be assayed. PHA is used as a mitogen which activates proliferation of T-lymphocytes. Thus, in one embodiment, said proliferation of PBMCs is the proliferation of T-lymphocytes, such as proliferation of PHA stimulated T-lymphocytes. The immunosuppressive activity of the drug product may be quantified as the decrease in proliferation of PHA stimulated T-lymphocytes.

Furthermore, the drug product may be assayed to measure prostaglandin E2 secreted by said drug product. Prostaglandin E2 (PGE2) is formed in a variety of cells from prostaglandin H2, which is synthesized from arachidonic acid by the enzyme prostaglandin synthetase. PGE2 has a number of biological actions, including vasodilation, both anti- and proinflammatory action, modulation of sleep/wake cycles, and facilitation of human immunodeficiency virus replication. PGE2 is active in inflammation, immune regulation, generation of fever, pain perception, protection of the gastric muscosa, fertility and parturition, as well as sodium and water retention. PGE2 is rapidly metabolized in vivo, the half-life of PGE2 in the circulatory system is approximately 30 seconds and normal plasma levels are 3-12 pg/mL. PGE2 is involved in the regulation of different stages of the immune response and different effector mechanisms of immunity. The drug product may constitutively produce PGE2, for example wherein the drug product is MSCs, and its proliferation is regulated by this prostaglandin through the differential activation of cAMP-dependent protein kinase isoforms. This production of PGE2 is sensitive to the local environment, where inflammatory signals stimulate its induction. During co-culture with immune cells, PGE2 production by drug product may be substantially increased and participates in the immunomodulatory effects of drug product. Moreover, the role of PGE2 in immunosuppressive effects depends on T-cell stimuli, as reported by Rasmusson et al. (Rasmusson et al., (2005) Exp. Cell. Res, 305 (1) (2005), pp. 33-41). PGE2 is effective in MSC inhibition of T cells activated by PHA rather than by alloantigens. The drug product may prevent lymphocyte activation and induce the inhibition of T-cell proliferation through the modulation of COX1/COX2 expression and ultimately PGE2 production. Therefore, it is possible use the amount of PGE2 secretion found in cell culture supernatants from co-cultures of peripheral blood mononuclear cells (PBMCs) and the drug product as a measure of immunosuppressive capacity. In one embodiment there is provided a method for in vitro prediction as disclosed herein, wherein said at least 2 assays comprise at least one assay measuring prostaglandin E2 secreted by said drug product in property b),In one embodiment, said at least one assay measuring prostaglandin E2 secreted by said drug product comprises measuring prostaglandin E2 secreted by said drug product when co-cultured with PBMCs, such as PHA stimulated PBMCs, such as PHA stimulated T-lymphocytes. It is to be understood that said PBMCs may be the patient's own immune cells.

In yet another assay, the HLA-G expression in the drug product, for example MSCs, may be measured. HLA-G has been identified as a naturally occurring tolerance-inducing molecule. It has restricted expression under physiological conditions but can be upregulated e.g. in response to IFNγ, IL-10 and PHA. The drug product, for example MSCs, may have low levels of intracellular HLA-G and express low levels of soluble HLA-G (sHLA-G) but stimulation with IFNγ or IL-10 will result in increased levels. Intracellular HLA-G expression may be assayed for example by flow cytometry (FACS) analysis and the release of sHLA-G may be assayed by for example ELISA.

In one embodiment there is provided a method for in vitro prediction as disclosed herein, wherein said at least 2 assays comprise at least one assay measuring HLA-G expression in said drug product in response to IFNγ, IL-10 and/or PHA in property b). Said IFNγ, IL-10 and/or PHA may be secreted or expressed by the patient's own immune cells.

In one embodiment there is provided a method for in vitro prediction as disclosed herein, wherein said at least 2 assays comprise at least one assay measuring the protein expression and/or cytokine expression of the patient's own immune cells in property a) and/or of the drug product in property b). For example, it may be of interest to evaluate the expression of interleukins, growth factors, interferon, tumor necrosis factors, colony stimulating factors and lipoproteins. Thus, in one embodiment said least one assay measuring the protein expression and/or cytokine expression measures the expression of one or several proteins or cytokines selected from the group consisting of interleukins, growth factors, interferons, tumor necrosis factors, colony stimulating factors and lipoproteins. In another embodiment, said at least one assay measuring the protein expression and/or cytokine expression measures the expression of one or several proteins or cytokines selected from the group consisting of IL-2, IL-4, IL-6, IL-8, IL-12, I L-12/13, IL-13, IL-17A, IL-21, IL-22, IL-29, IL-31, TGFβ, VEGF, FGF, GM-CFS, IFNα, IFNγ, apo E and TNFα; such as the group consisting of IL-6, IL-8, GM-CSF and TGFβ; such as the group consisting of at least IL-6. In one particular embodiment, the expression of at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as all 19 of said proteins and/or cytokines is measured.

Furthermore, the skilled person will appreciate the expression of said proteins and/or cytokines may be measured in the absence of any stimuli and/or in the present of at least one stimulus. In one embodiment, said stimuli is an immune response modifying stimuli. Non-limiting examples of said immune response modifying stimuli include PBMCs, stimulated PBMCs (such as PBMCs stimulated with PHA), MO, gamma-aminobutyric acid (GABA), interferon gamma (IFNγ) and other. Thus in one embodiment, said immune response modifying stimuli is selected from the group consisting of PBMCs, stimulated PBMCs, PBMCs stimulated with PHA, MO, GABA, IFNγ. In one embodiment, said stimuli is GABA or IFNγ. In one embodiment, there is provided a method for in vitro prediction as disclosed herein, wherein the stimuli is selected from the group consisting of polyinosinic: polycytidylic acid (Poly I:C), resiquimod (r848), GABA and IFNγ, such as the group consisting of Poly I:C and IFNγ. In one embodiment, said stimuli is PBMCs, such as stimulated or unstimulated PBMCs, such as PHA stimulated PBMCs, such as PHA stimulated T-lymphocytes.

The skilled person appreciates that said assays may be combined to obtain a specific assay combination of interest depending to the desirable properties of the patient's own immune cells and of the drug product assayed. The assays may be selected independently of each other.

It will be appreciated that the results from said assays/analyses may provide information about inflammatory status and probability of if it is possible to lessen or revert said status by treatment of the patient in need thereof with the drug product. Therefore, the results from said assays/analyses may be useful for evaluation of therapeutic options.

Thus, in one embodiment there is provided a method for in vitro prediction as disclosed herein, wherein an inflamed state is predicted to be reverted if the results in a) and/or b) show at least one of 1) a decrease of proinflammatory immune cells proliferation; 2) a decrease in secretion of proinflammatory molecules; 3) switching of immune cells from a proinflammatory to an anti-inflammatory phenotype; 4) apoptosis of CD8+ T cells; 5) apoptosis of memory B cells; and 6) apoptosis of memory T cells. In particular, said inflamed state may be predicted to be reverted if the results in a) and/or b) show that at least two, at least three, at least four, at least five or all six of the conditions 1)-6) are shown. In one embodiment there is provided a method for in vitro prediction as disclosed herein, wherein an inflamed state is predicted to be reverted if the results in a) and/or b) show at least one of 1) a decrease of proinflammatory immune cells proliferation; 2) a decrease in secretion of proinflammatory molecules; and 3) switching of immune cells from a proinflammatory to an anti-inflammatory phenotype. In particular, said inflamed state may be predicted to be reverted if the results in a) and/or b) show that at least two or all three the conditions 1)-3) are fulfilled. In particular, said at least two conditions may be condition 1) and 2), condition 2) and 3), or condition 1) and 3).

It may be beneficial to also analyze serum or other fluid or tissue originating from the patient for preexisting antibodies, antigens, microbes, with affinity to the drug product. Of particular interest may be the detection of preexisting antibodies with affinity to the drug product. Preexisting antibodies are expected to result in a faster clearing of the drug product in vivo. If a patient is found have preexisting immunization, this analysis will be followed by a secondary analysis for specificity towards the drug product.

Thus, in one embodiment there is provided a method for in vitro prediction as disclosed herein, wherein in property c) serum from the patient is analyzed for the presence of HLA antibodies; such as HLA antibodies without specific affinity for the drug product and/or HLA antibodies with specific affinity for the drug product. As used herein, the term "specific affinity" refers to a the property of the HLA antibodies to bind the drug product, thus HLA antibodies with specific affinity for the drug product bind the drug product and HLA antibodies without specific affinity for the drug product do not bind the drug product. To clarify, a selected threshold $K_D$-value of the interaction/binding between the HLA antibodies and the drug product may be used to characterize the interaction, for example said threshold value may be $10^{-2}$M, $10^{-3}$M, $10^{-4}$M, $10^{-6}$M, $10^{-7}$M, $10^{-7}$M, $10^{-8}$M or $10^{-10}$M. Thus, a HLA antibody capable of binding the drug product with at most said threshold $K_D$-value of the interaction is considered to exhibit specific affinity for the drug product while a HLA antibody capable of binding the drug product with at higher $K_D$-value of the interaction than said threshold $K_D$-value of the interaction is considered not to exhibit specific affinity for the drug product (in other words it is a HLA antibody without specific affinity for the drug product). The skilled person is familiar with methods, for example SPR-analysis, known in the art for the determination of $K_D$-values for antibody antigen interactions/binding. In one embodiment, said serum from the patient is analyzed for the presence of HLA antibodies with specific affinity for the drug product. In one embodiment, no presence of HLA antibodies is the most desirable result and the presence of HLA antibodies with specific affinity for the drug product is the least desirable result. No presence of HLA antibodies with specific affinity for the drug product is indicative of that the patient is eligible for treatment with the drug product. For clarity, as used herein the term "HLA antibodies" refers to antibodies with affinity for HLA, also referred to as anti-HLA antibodies. These terms are used interchangeably in the present disclosure.

In one embodiment of the present method, said at least two assays comprise an assay measuring prostaglandin E2 secreted by said drug product in property b) and an assay measuring the effect of said drug product on the proliferation of said patient's own peripheral blood mononuclear cells (PBMCs) in property a). In one embodiment, said at least two assay comprise an assay measuring prostaglandin E2 secreted by said drug product in property b) and an assay measuring the effect of said drug product on the proliferation of said patient's own peripheral blood mononuclear cells (PBMCs) in property a) and assay measuring the indoleamine-2,3-dioxygensase (I DO) activity in property b). Said indoleamine-2,3-dioxygensase (I DO) activity maybe measure as the ratio of kynurenine/tryptophan or the plasma concentration of kynurenine as described above.

The present method comprises an overall assessment based on evaluation of said at least properties a) and b) or at least properties b) and c) by at least two assays. The overall assessment is based on a compilation of results from individual assays which results are translated to an individual score value for each tested assay and drug product/patient own immune cell tested. Said an individual score value is next complied to a total score value upon which the prediction is based.

Thus, in one embodiment there is provided a method for in vitro prediction as disclosed herein, wherein an individual score value is assigned to the results of each functional and/or potency assay evaluating at least properties a) and b) or at least properties b) and c) by at least two assays and wherein said the overall assessment comprises allocating a total score value of the in vitro prediction. In one embodiment, said individual score value is assigned based on a comparison of the assay result to at least one reference result. In another embodiment, said individual score value is assigned based on a comparison of the assay result to an absolute value. In the case when an individual score value is indicative of more desirable assay result, a higher total score value is indicative of more desirable properties in respect to the patient's own immune system response to the drug product treatment. Alternatively, in the case when a lower individual score value is indicative of an more desirable assay result, a lower total score value is indicative of more desirable properties respect to the patient's own immune system response to the drug product treatment. The skilled person will appreciate that the ranking score value system and/or the total score value system may be modified without departing from the scope of the present disclosure.

In one embodiment there is provided a method for in vitro prediction as disclosed herein, wherein in the case of a higher individual score value being indicative of more desirable assay result, a higher total score value is indicative of in vitro prediction of desirable in vivo efficacy; or wherein in the case of a lower individual score value being indicative of more desirable assay result, a lower total score value is indicative of in vitro prediction of desirable in vivo efficacy. In one embodiment said total score value may be an additive total score value or a weighed total score value, as discussed below. In one embodiment there is provided a method for in vitro prediction as disclosed herein, wherein said in vitro prediction predicts the likelihood of minimizing undesirable immunological reaction in said patient to said drug product. For example, said in vitro prediction may predict the likelihood of no undesirable immunological effects in said patient to said drug product.

In one embodiment there is provided a method for in vitro prediction as disclosed herein, wherein said in vitro prediction predicts the likelihood of therapeutically desirable response in said patient of treatment with said drug product. In particular, said in vitro prediction may predict if the patient will exhibit a high response, a response, a low response or no response to treatment with said drug product. For clarity a patient who is predicted to exhibit a high response or a response may be recommended treatment with said drug product as a therapeutic option. The skilled person will appreciate that the quantification of a response may be adapted to the readout and assay used. As a non-limiting example, wherein HbA1c is a readout of patient response, it may be considered that a 10% or higher HbA1c decrease after 1 month and maintained decrease after at least 3 months is a high response; a 5-10% HbA1c decrease after 1 month and maintained decrease after at least 3 months is a response, and less than 5% HbA1c decrease after 1 month and maintained decrease after at least 3 months is a low response.

Said in vitro prediction may predict if the patient will exhibit a response (in other words be responder) or no response (in other words be a non-responder) to treatment with said drug product. For clarity a patient who is predicted to exhibit a response may be recommended treatment with said drug product as a therapeutic option. For example, reference donors with known clinical outcome may be used and patients with higher total score than said reference are predicted to have better clinical response than said reference donor (thus higher response) while patients with lower total score than said reference are predicted to have lower clinical response than said reference donor (thus lower response). For example, the reference donor may be a threshold reference donor. In this case, a higher total score than that of the threshold reference donor would be indicative of that the patient is recommended for treatment with the drug product and conversely a lower total score than that of the threshold reference donor would be indicative of that the patient is not recommended for treatment with the drug product. To clarify, the above example is based on the case wherein higher individual score values are indicative of more desirable assay results and thus a higher total score value will be indicative of a more desirable prediction outcome, in other words higher response. The skilled person will appreciated that in the case wherein lower individual score values are indicative of more desirable assay results and thus a lower total score value will be indicative of a more desirable prediction outcome, in other words higher response, and that said example would thus be adapted accordingly.

The total score value may be an additive score value obtained by addition of ranking score values for each assay in property a) and/or b) and/or c). Alternatively, the total score value may be a weighed total score value, obtained by 1) assigning a weight to the ranking score value for each assay and 2) adding the weighed ranking score values for each assay in property a) and/or b) and/or c). In this way it is possible to allocate a relatively higher weight (or importance) to one or several assay result of choice compared to the remaining assay results. The skilled person will appreciate that one or several assay results may be weighed and the weight allocated to each assay result may be chosen independently. Thus, in one embodiment there is provided a method as disclosed herein, wherein said additive total score value obtained by addition of individual score values for each assay. In another embodiment, said total score value is a weighed total score value obtained by 1) assigning a weight to the individual score value for each assay and 2) adding the weighed individual score values to obtain a weighed total score value. In principle, the results of assay 1 may be assigned a weight X, the results of assay 2 may be assigned a weigh Y, the results of assay 3 may be assigned a weight Z etc., wherein X, Y, Z etc. may be the same or different numerical values. The total score value may be obtained by calculating the sum of [individual score value from assay 1]×X+[individual score value from assay 2]×Y+[individual score value from assay 3]×Z etc. for each assay which is part of the analysis. As illustrative non-limiting example, the individual score vale for proliferation index assay may be assigned double the weight of the individual score value of the IDO assay and of the PGE2 assay, such that the total score value is calculated as the sum of: 2 times the individual score vale for proliferation index assay+1 time individual score vale for IDO assay+1 time individual score vale for PGE2 assay. The skilled person will appreciate that other weights may be assigned to these and other assay. To clarify, in the case wherein higher individual score values are indicative of more desirable assay results, a higher total score value will be indicative of a more desirable prediction outcome, for example a higher likelihood of in vivo efficacy of treatment with the drug product, or a lower likelihood of in vivo adverse immunological reaction to the drug product. It will be understood that in the case wherein lower individual score values are indicative of more desirable assay results, a lower total score value will be indicative of a more desirable prediction outcome.

It will be appreciated that the present invention as disclosed herein, is envisioned to be particularly useful for the prediction of the in vivo efficacy in a patient of treatment with a drug product, such as a patient who suffers from a disorder which may be subject to treatment with the drug product. Thus, in one embodiment of said method, wherein said patient suffers from a disorder subject to treatment with the drug product. For example, the clinician may choose treatment with said drug product as a therapeutic option. It is envisioned that the method as disclosed herein will be useful for prediction of in vivo efficacy when said disorder is selected from autoimmune disorders, inflammatory disorders and transplantation associated complications, for example a disorder selected from Achlorhydria, Acute hemorrhagic leukencephalitis, Addison's Disease, Alopecia Areata, Amyo lateral Sclerosis, Anemia, Pernicious Anti-Glomerular Basement Membrane Disease, Antiphospholipid Syndrome, Aplastic Anemia, Arteriosclerosis, Atopic Allergy, Autoimmune Atrophic Gastritis, Autoimmune Hearing Loss, Autoimmune hemolytic anemia, Autoimmune hypoparathyroidism, Autoimmune hypophysitis, Autoimmune Lymphoproliferative, Autoimmune Myocarditis, Autoimmune oophoritis, Autoimmune orchitis, Autoimmune Polyendocrinopathy-Candidiasis-Ectodermal-Dystrophy, Autoimmune Syndrome Type II, Polyglandular, Behcet Syndrome, Celiac Disease, Chagas Disease, Cholangitis, Sclerosing, Chronic Inflammatory Demyelinating Polyneuropathy, Chronic lymphocytic thyroiditis, Churg-Strauss Syndrome, Colitis, Ulcerative, Crohn's disease, Cryoglobulinemia, Cushing Syndrome, Dementia, Dermatitis Herpetiformis, Dermatomyositis, Diabetes Mellitus type 1 and type 2, Diffuse Cerebral Sclerosis of Schilder, Encephalomyelitis, Autoimmune, Experimental (EAE), Epidermolysis Bullosa Acquisita, Erythematosis, Felty's Syndrome, Glomerulonephritis (IGA), Glomerulonephritis Membranous, Goodpasture Syndrome, Graves' Disease, Guillain-Barre Syndrome, Hamman-Rich syndrome, Hepatitis Autoimmune, Hepatitis Chronic Active, Idiopathic thrombocytopenia, Inflammatory Bowel Diseases, Insulin resistance—type B, Lambert-Eaton Myasthenic Syndrome, Lens-induced uveitis, Lichen Sclerosus et Atrophicus, Lupus Erythematosus Discoid, Lupus Erythematosus Systemic, Lupus Hepatitis, Lupus Nephritis, Lymphopenia, Meniere's Disease, Mixed Connective Tissue Disease, Mooren's ulcer, Mucocutaneous Lymph Node Syndrome, Multiple Sclerosis, Myasthenia Gravis, Myelitis Transverse, Myocarditis, Narcolepsy, Neuritis Autoimmune Experimental, Neuromyelitis Optica, Oculovestibuloauditory syndrome, Ophthalmia Sympathetic, Opsoclonus-Myoclonus Syndrome, Pancreatitis, Parkinsons's disease, Pemphigoid Bullous, Pemphigus foliaceous, Pemphigus Vulgaris, Polyarteritis Nodosa, Polychondritis Relapsing, Polyendocrinopathies Autoimmune, Polymyalgia Rheumatica, Polyradiculoneuropathy, Primary biliary cirrhosis, Psoriasis, Purpura Thrombocytopenic Idiopathic, Raynauds, Reiter Disease, Rheumatic Fever, Rheumatoid Arthritis, Sarcoidosis, Scleroderma, Sjogren's Syndrome, Spondylitis Ankylosing, Stiff-Person Syndrome, Still's Disease Adult Onset, Takayasu's Arteritis, Temporal Arteritis, Thyrotoxicosis, Type B Insulin Resistance, Uveomeningo-encephalitic Syndrome,Wegener's disease and transplantation associated complications, such as renal transplantation associated complications, heart transplantation associated complications, liver transplantation associated complications and lung transplantation associated complications.

In particular, said method for prediction as disclosed herein is envisioned to be particularly useful for prediction of in vivo efficacy when said disorder is selected from such as autoimmune diabetes, amyotrophic lateral sclerosis or renal transplantation associated complications. Thus, in one embodiment of the method as disclosed herein, said disorder is selected from autoimmune disorders, inflammatory disorders and transplantation associated complications, such as autoimmune diabetes, amyotrophic lateral sclerosis or renal transplantation associated complications.

In a second aspect of the present disclosure, there is provided a method of treatment of a patient in need thereof, wherein said patient is treated with a drug product if said drug product is predicted to be efficacious in vivo based on the method for in vitro prediction of said in vivo efficacy as disclosed herein. In one embodiment, said treatment is by administration of a therapeutically effective amount of said drug product to said patient. In one embodiment, said patient is in need of immunosuppressive treatment. In particular, said patient may be suffering or may be at risk of suffering from a disorder selected from the group consisting of autoimmune disorders, inflammatory disorders and transplantation associated complications, such as the group consisting of autoimmune diabetes, amyotrophic lateral sclerosis or renal transplantation associated complications. In one embodiment, said patient is an animal, such as a mammal, such as a human. Said drug product may be selected from the group consisting of whole cells, such as live cells, dead cells, or lyophilized cells; extracellular vesicles obtained from cell culture; exosomes; and conditioned media; such as the group consisting of MSCs, such as live MSCs, dead MSCs, or lyophilized MSCs; extracellular vesicles obtained from MSCs cultures; and exosomes from MSCs.

In a third aspect, there is provided a drug product for use in treatment and/or prevention of a disorder, wherein the drug product is predicted to be efficacious in vivo based on the method for in vitro prediction of said in vivo efficacy as disclosed herein. In particular, said disorder may be selected from the group consisting of autoimmune disorders, inflammatory disorders and transplantation associated complications, such as the group consisting of autoimmune diabetes, amyotrophic lateral sclerosis or renal transplantation associated complications. Said drug product may be selected from the group consisting of whole cells, such as live cells, dead cells, or lyophilized cells; extracellular vesicles obtained from cell culture; and exosomes; such as the group consisting of MSCs, such as live MSCs, dead MSCs, or lyophilized MSCs; extracellular vesicles obtained from MSCs cultures; and exosomes from MSCs.

In a fourth aspect, there is provided drug product formulation for use in treatment and/or prevention of a disorder, wherein the drug product is predicted to be efficacious in vivo based on the method for in vitro prediction of said in vivo efficacy as disclosed herein. In particular, said disorder may be selected from the group consisting of autoimmune disorders, inflammatory disorders and transplantation associated complications, such as the group consisting of autoimmune diabetes, amyotrophic lateral sclerosis or renal transplantation associated complications. Said drug product may be selected from the group consisting of whole cells, such as live cells, dead cells, or lyophilized cells; extracellular vesicles obtained from cell culture; and exosomes; such as the group consisting of MSCs, such as live MSCs, dead MSCs, or lyophilized MSCs; extracellular vesicles obtained from MSCs cultures; and exosomes from MSCs.

In a fifth aspect of the present disclosure there is provided an in vitro use of a drug product for predictive purposes. Thus, in one aspect of the present disclosure there is provided an in vitro use of a drug product for the in vitro prediction of the efficacy of said drug product in vivo. In one embodiment, said in vitro prediction is according to the method for in vitro prediction of in vivo efficacy as defined in the present disclosure. In one embodiment, said in vitro use comprises analysis of properties a) and/or b) by at least 2 assays, wherein said properties are:
  a) The in vitro reaction of said patient's own immune cells when exposed to the drug product with and/or without stimulation; and
  b) The reaction of said drug product when exposed to said patient's own immune cells.

The skilled person will appreciate that any one of the assays described in the context of the first aspect, is equally applicable to this fifth aspect. The details of said assays will not be repeated here for the sake of brevity.

In one embodiment of the in vitro use as disclosed herein, said drug product is selected from the group consisting of isolated whole cells (such as live cells, dead cells, or lyophilized cells); extracellular vesicles obtained from cell culture; and exosomes. In one embodiment said drug product is selected form the group consisting of isolated MSCs, such as live MSCs, dead MSCs, or lyophilized MSCs; extracellular vesicles obtained from MSCs cultures; and exosomes from MSCs. In one embodiment, said cells are live cells, such as live MSCs. In one embodiment, said cells are isolated live cells, such as isolated live MSCs. In one particular embodiment, said MSCs are an allogeneic MSC population, such as an isolated allogeneic MSC population. In one particular embodiment, said MSCs are a pooled allogeneic MSC population, such as a pooled isolated allogeneic MSC population.

In one embodiment, said in vitro use as disclosed herein is for making a patient specific treatment decision. For example said decision may be administering the patient said drug product or not administering said drug product, based on if said prediction recommends said treatment of not. Said in vitro prediction may be; treatment highly recommended, treatment recommended; consider treatment or treatment not recommended. It will be appreciated that the medical professional will make a treatment decision or treatment recommendation based on an overall assessment of the patient's disease status, which overall assessment may include the prediction as disclosed herein. Said in vitro use as defined herein, is considered particularly useful when the patient is in need of immunosuppressive treatment. Thus, in one embodiment of said in vitro use as disclosed herein, said patient is in need of immunosuppressive treatment. Said patient may be suffering or may be at risk of suffering from a disorder selected from autoimmune disorders, inflammatory disorders and transplantation associated complications. In one embodiment, said disorder is autoimmune diabetes. In one embodiment, said disorder is amyotrophic lateral sclerosis. In one embodiment, said disorder is renal transplantation associated complications.

The skilled person will appreciated that any embodiments disclosed in the context of the first aspect are equally applicable to the present aspect and will not be repeated there merely for the sake of brevity.

In yet another related aspect, there is provided a system for predicting the efficacy of a drug product prior to treatment of a patient in need thereof with said drug product, comprising the drug product and a total score based on results from at least 2 assays where the patient's own immune cells have been exposed in vitro to said drug product and wherein said prediction comprises the method for prediction as defined in the present disclosure. As explained in the context of the first aspect a total score may be an additive total score or a weighed total score. Said total score may be obtained and calculated based on individual scores as described in relation to the first aspect disclosed herein. It will be appreciated that the embodiments as disclosed in relation to the first aspect as disclosed herein are equally applicable to the present aspect and will not be repeated there for the sake of brevity.

In one particular embodiment of said aspect, a system as disclosed herein is provided, wherein said drug product is selected from the group consisting of isolated whole cells, (such as live cells, dead cells, or lyophilized cells); extracellular vesicles obtained from cell culture; and exosomes; such as the group consisting of isolated MSCs, such as live MSCs, dead MSCs, or lyophilized MSCs; extracellular vesicles obtained from MSCs cultures; and exosomes from MSCs. In one embodiment, said drug product comprises or is live cells, such as live MSCs. In one embodiment, said drug product comprises or is isolated live cells, such as isolated live MSCs. In one particular embodiment, said MSCs are an allogeneic MSC population, such as a pooled allogeneic MSCs population. In one embodiment, said MSCs are an isolated allogeneic MSC population, such as an isolated pooled allogeneic MSCs population. In one embodiment of said system, the prediction comprises the method for in vitro prediction of the in vivo efficacy in a patient of treatment with a drug product as disclosed herein.

In another aspect, there is provided a drug product for use in treatment and/or prevention of a disorder, wherein the drug product is predicted to be efficacious in vivo based on the method for in vitro prediction of said in vivo efficacy as defined herein. In one embodiment, there is provided a drug product for use as described herein, wherein said disorder is selected from the group consisting of autoimmune disorders, inflammatory disorders and transplantation associated complications. In one particular embodiment, drug product is selected from the group consisting of isolated whole cells, (such as live cells, dead cells, or lyophilized cells); extracellular vesicles obtained from cell culture; and exosomes; such as the group consisting of isolated MSCs, such as live MSCs, dead MSCs, or lyophilized MSCs; extracellular vesicles obtained from MSCs cultures; and exosomes from MSCs. In one embodiment, said drug product comprises or is live cells, such as live MSCs. In one embodiment, said drug product comprises or is isolated live cells, such as isolated live MSCs. In one particular embodiment, said MSCs are an allogeneic MSC population, such as a pooled allogeneic MSCs population. In one embodiment, said MSCs are an isolated allogeneic MSC population, such as an isolated pooled allogeneic MSCs population. In particular, said drug product may be an allogeneic MSC population as defined herein.

While the invention has been described with reference to various exemplary aspects and embodiments, it will be understood by those skilled in the art that various changes may be made and equivalents may be substituted for elements thereof without departing from the scope of the invention. Therefore, it is intended that the invention not be limited to any particular embodiment contemplated, but that the invention will include all embodiments falling within the scope of the appended claims. The invention will be further illustrated by the following non-limiting Examples.

BRIEF DESCRIPTION OF THE FIGURES

FIG. 1 is a graphical representation of the HbA1c levels in six patients treated with the drug product, whereof three patients were predicted to be responders and three patents were predicted to be non-responders. X-axis shows the time in months and Y-axis shows change in HbA1c concentration (mmol/mol) from before treatment and (average of baseline and screening visit value) and after treatment as indicated on the X-axis. Negative value of change in HbA1c concentration is evidence of effect. Patient 5 has the largest decrease, Patient 1 and 2 have a measured effect over more than 3 months, whereas Patient 3, 4 and 6 show limited or no effect of treatment.

EXAMPLES

The present non-limiting Examples describe the assays and the compiling of data from the assays in the Prediction Algorithm.

Example 1

This example describes the process of isolation of the patient's immune cells (also known as peripheral blood mononuclear cells, PBMCs) from a venous blood sample.

Material and Methods

A minimum of 10 ml peripheral blood is collected from the patient, usually from the arm vein with a vacutainer containing Heparin. A Lymphoprep™ kit is used for isolation of mononuclear cells (PBMCs), according to manufacturer's instructions (Stem Cell Technologies, cat no. 07801). PBMCs are counted after staining with Turk colour and then suspended in media, usually $2-20 \times 10^6$ cells/ml in multiple aliquots in respectively.

Results

Immune cells to be used as reference donors are can be achieved from buffy coat purchased from blood banks. Since the donor variability is the scope of the assay, large batches from each reference donor is desirable. The sample is aliquoted for repeated usage in analysis. New reference donors are compared with old reference donors (or more correctly, donors of who's cells the number of aliquots available is low). In Table 1 below, the yield of 7 consecutive reference donor lymphopreparations is presented.

TABLE 1

Summary of 7 consecutive donor samples processed.

| donors | blood volume (buffy coat), ml | PBMC, millions |
|---|---|---|
| PBMC 1 | 45 | 496 |
| PBMC 2 | 45 | 796 |
| PBMC 3 | 50 | 561 |
| PBMC 4 | 46 | 647 |
| PBMC 5 | 43 | 397 |
| PBMC 6 | 45 | 512 |
| PBMC 7 | 45 | 522 |

The amount of cells recovered from a normal blood sample, i.e. the patient's own immune cells, is more limited. Table 2 below shows the number of cells from 6 patients, collected at two occasions.

TABLE 2

Summary of 6 consecutive patient samples processed at two occasions separated by approximately 1 month.

| Patient | Occasion | Blood volume, ml | PBMC, millions |
|---|---|---|---|
| PAT01 | #1 | 22.5 | 15 |
|  | #2 | 22.5 | 6.3 |
| PAT02 | #1 | 22 | 66 |
|  | #2 | 24 | 15 |
| PAT03 | #1 | 26 | 22.6 |
|  | #2 | 24.5 | 18.5 |
| PAT04 | #1 | 26.5 | 17 |
|  | #2 | 27.5 | 24.6 |
| PAT05 | #1 | 25 | 13.7 |
|  | #2 | 26.5 | 16.7 |

TABLE 2-continued

Summary of 6 consecutive patient samples processed at
two occasions separated by approximately 1 month.

| Patient | Occasion | Blood volume, ml | PBMC, millions |
|---------|----------|------------------|----------------|
| PAT06   | #1       | 27               | 18.5           |
|         | #2       | 24               | 20             |

Example 2

This Example describes the storage, cryopreservation, thawing and culturing of the patient's immune cells in absence and presence of the drug product
Material and Methods:

The cell suspension containing the patient's PBMCs or reference donor is prepared for cryopreservation by addition of 10% DMSO at +4° C. and then frozen in cryotubes according to a pre-set temperature curve using a controlled rate freezer. The cryotubes are then moved to a liquid nitrogen tank and stored in the gas phase until needed. When thawing it is important to quickly thaw and dilute the PBMCs in culture medium to minimise the toxic effects from dimethyl sulfoxide (DMSO). The cryotube vials with the patient's PBMCs are taken out from the liquid nitrogen tank. Then the cryo tubes are thawed in 37° C. water bath and transferred to a 15 ml tube containing 11 ml thawing medium. The 15 ml tubes are centrifuged at 350 g for 8 min at room temperature (RT) after which the supernatant is removed. The washing procedure is repeated by again filling the 15 ml tube with 13 ml thawing media and centrifuging at 350 g for 8 min at RT. (total 2× washing). The supernatant is removed and 1 ml working media is added. The cells are then counted.
Results The patient's own immune cells (PBMCs) are now ready for use in the assays according to Example 3, Example 4 and Example 5. Cell viability post thaw is consistently >90% as decided by 7AAD staining.

Example 3

The present Example describes how the patient's own immune cells (PBMCs and microglia cells) are affected by the drug product.
Assay 1: Proliferation Assay
Material and Methods:

This method is used to quantitatively measure the immunosuppressive effect that the drug product has on the proliferation of the patient's own immune cells (PBMCs). Mixed lymphocyte reactions are frequently used to demonstrate the immunosuppressive activity of a certain drug product, however, in this case we know the potency of the drug product, as it is tested on a number of donors used as References (see Table 1), and the assay is instead conducted to evaluate the possible effectivity and safety associated with administering the drug product to this particular patient, considering the patient's disorder. Phytohaemagglutinin (PHA) is used as a mitogen which activates proliferation of T-lymphocytes. The immunosuppressive activity of the drug product is quantified as the decrease in proliferation of PHA stimulated T-lymphocytes.

Culturing and Carboxyfluorescein succinimidyl ester (CFSE) priming: 500 µl of working medium (RPM11640 (ThermoFisher Scientific, cat no. 12633012+2 mM Glutamax (ThermoFisher Scientific, cat no. 35050061)+100 U/ml Pest (ThermoFisher Scientific, cat no. 15140122)+10% FBS (ThermoFisher Scientific, cat no. 16140071) MSC ($2\times10^5$ cells/well) is seeded in 12-well cell culture plates. If 96-well plates are used, the amount of MSC seeded is 48 000/well. The plates are incubated at 37° C.+5% $CO_2$ for 2 hours for plastic adherence of cells. PBMCs are then added at a 1:5 ratio, i.e. $1\times10^6$ cells/12-well or $2.4\times10^5$ cells/96-well plate and further incubated for 72 hours before flow cytometry analysis. PBMCs from donated peripheral blood are used in the reference samples, see Table 3.

TABLE 3

Summary of donor samples analysed for proliferation,
i.e. proliferation index, in absence or presence of
two different batches of drug product (TB1 and CB1).

| Reference donor | PI with PHA | PI with MSC batch TB1 | PI with MSC batch CB1 |
|-----------------|-------------|------------------------|------------------------|
| PBMC 1          | 1.85        | —                      | —                      |
| PBMC 2          | 1.16        | —                      | —                      |
| PBMC 3          | 2.00        | 1.11                   | —                      |
| PBMC 4          | 1.72        | 1.10                   | 1.10                   |
| PBMC 5          | 1.64        | 1.10                   | —                      |
| PBMC 6          | 2.04        | 1.10                   | 1.10                   |
| PBMC 7          | 1.63        | 1.03                   | 1.03                   |

Analysis: CFSE positive cells are analyzed by flow cytometry (Merck, Guava easyCyte 5HT or Accuri C6 Plus). CFSE histogram includes three or four peaks and the first top from the right represents undivided cells (G0). The following tops show different generations (G1-G4). Proliferation Index (PI) is calculated as the total number of cells of all generations divided by the number of parent cells that entered cell division.
Result The average PI for the patient's own immune cells is used to score the impact that the drug product had in terms of decreasing proliferation in comparison to reference donors of PBMC. A desirable result for the Proliferation index is close to 1, which indicates that the patient's own immune cells are inactivated and no longer proliferating when co-cultured with the drug product. The score, assigned either based on ranking or predefined scores, is later used in the Prediction Algorithm (see Example 6). The proliferation index of patient's own cells may significantly differ between patients. A delta proliferation index can be used as read out value, i.e. proliferation index of the patient's own cells in presence of PHA and drug product in subtracted with the proliferation index of the patient's own cells in presence of PHA. The larger decrease in delta PI, the higher effect of the drug product in the specific assay.

TABLE 4

Illustrative example of ranking score based on proliferation index. Four
reference donors are included in the assay and the sample is evaluated
in relation to these donors. The references and the sample are scored
based on the proliferation index and the lowest will score 5, and the
highest (least desirable proliferation index) will score 1.

| Donor | Proliferation Index | Score |
|-------|---------------------|-------|
| Ref1  | 1.04                | 5     |
| Ref2  | 1.10                | 4     |
| Ref3  | 1.22                | 2     |

TABLE 4-continued

Illustrative example of ranking score based on proliferation index. Four reference donors are included in the assay and the sample is evaluated in relation to these donors. The references and the sample are scored based on the proliferation index and the lowest will score 5, and the highest (least desirable proliferation index) will score 1.

| Donor | Proliferation Index | Score |
| --- | --- | --- |
| Ref4 | 1.35 | 1 |
| Sample | 1.12 | 3 |

Alternatively, the scoring of the sample could be based on predefined scores for specified ranges of Proliferation indexes as shown in Table 5. The sample would score 3 if using this scoring.

TABLE 5

Scoring table of proliferation index to be used in the prediction algorithm.

| Proliferation Index range | Score |
| --- | --- |
| <1.05 | 5 |
| 1.06-1.10 | 4 |
| 1.11-1.15 | 3 |
| 1.16-1.20 | 2 |
| 1.21-1.30 | 1 |
| >1.31 | 0 |

Assay 2: Microglia
Material and Methods:

The biopsy is of approximately 1-2 grams of tissue from the patient is needed as starting material. First the tissue is washed in Hanks' Balanced Salt Solution (HBSS). Tissue is diced into small pieces, vessels and meninges are removed. The pieces are then transferred to a 50 mL falcon tube containing 10 mL enzyme dissociation mix (10 U/mL DNase (Invitrogen, CA, USA) and 2.5 U/mL papain (Worthington, NJ, USA) in Hibernate-A medium (Gibco, CA, USA)) per gram of tissue. This is subsequently incubated for 10 minutes at 37° C. with gentle rotation. The tissue is then removed from the incubator, gently triturated to aid digestion and returned to the incubator for a further 10 minutes. Dissociation is slowed by adding an equal volume of Dulbecco's modified eagle medium: Nutrient mixture F-12 (DMEM/F12; Gibco, CA, USA) with 1% B27 (Gibco, CA, USA) and the cell suspension is passed through a 70 μm cell strainer (Bector Dickinson, NJ, USA). Cells are centrifuged at 160×g for 10 minutes, the supernatant discarded and resuspended in 20 mL neural precursor cell (NPC) proliferation media (DMEM/F12 with 1% B27, 1% GlutaMAX (Gibco, CA, USA), 1% penicillin-streptomycin-glutamine (PSG; Gibco, CA, USA), 40 ng/mL fibroblast growth factor-2 (FGF-2; Peprotech, NJ, USA), 40 ng/mL epidermal growth factor (EGF; Peprotech, NJ, USA) and 2 pg/mL heparin (Sigma, MO, USA)). The cell suspension is transferred to a T75 tissue culture flask (Nunc, Roskilde, Denmark) and incubated overnight at 37° C. with 5% CO2.

Tissue culture flask are tapped firmly to remove non-adherent or loosely-adherent cells. The flask containing the adherent cells is washed twice with NPC proliferation media and 15 mL of microglial culture media is added (DMEM/F12 with 10% fetal bovine serum (FBS; Moregate, QLD, Australia) and 1% PSG).

Microglia are maintained in this media for up to 1 week at 37° C. with 5% CO2. When cultured as described above, microglial yields of 2-300,000 cells/gram of tissue can be expected.

To harvest cells for plating, culture media is removed and T75 tissue culture flasks are washed with phosphate buffered saline (PBS). 3 mL of 0.25% trypsin-1 mM ethylenediaminetetraacetic acid (EDTA; Gibco, CA, USA) was added for five minutes at 37° C. with 5% CO2. Microglia attach firmly to the T75 tissue culture flasks and to aid microglial detachment cells are gently scraped with a rubber cell scraper (Falcon, MA, USA). Trypsin is neutralized by addition of microglia culture media and cells counted using a hemocytometer. Cells are plated at 5,000 cells/well for 96 well plates or 25,000 cells/well for 24 well plates. Cells are allowed to attach overnight before utilization for experiments (Rustenhoven et al., Scientific Reports (2016) Sci Rep; 19371). The patient's own immune cells (microglia) are stimulated with IFNgamma 100 ng/ml for 24 hours. The media is removed, and the cells are washed twice with PBS. The drug product is added to the cells and incubated for 3 days with the drug product. In the case of the drug product being MSC based, the cell concentration is 1:1.

Unstimulated microglia are compared with stimulated microglia and stimulated microglia co-cultured with drug product. The cells are analyzed by flow cytometry for the markers: CD11b, CD14, CD68 and CD200r.

Results:

A favorable response to the drug product is decrease expression of CD14 which is a surrogate marker for potency.

TABLE 6

Illustrative example of ranking score based on expression. Four reference donors are included in the assay and the sample is evaluated in relation to these donors. The references and the sample are scored based on the expression of CD14 and the reference/sample with the highest expression will score 5, and the lowest (least desirable CD14 expression) will score 1.

| Donor | CD14+ | Score |
| --- | --- | --- |
| Ref1 | 5 | 5 |
| Ref2 | 10 | 4 |
| Ref3 | 35 | 2 |
| Ref4 | 42 | 1 |
| Sample | 31 | 3 |

Alternatively, scoring of the patient's own immune cell response to the drug product is based on a predefined scoring table.

TABLE 7

Scoring table of predefined levels of expression assigning a score to the sample to be used in the prediction algorithm

| CD14+ | Score |
| --- | --- |
| >51 | 1 |
| 41-50 | 2 |
| 21-40 | 3 |
| 6-20 | 4 |
| <5 | 5 |

Example 4

The present Example describes assays of evaluating how efficacious the patient's own immune cells will alter the drug product protein expression when the drug product is based on mesenchymal stromal/stem cells.

Assay 3: Prostaglandin E2
Material and Methods:

A Prostaglandin E2 (PGE2) assay is used to evaluate secretion of PGE2 from drug product when co-cultured with peripheral blood mononuclear cells (PBMCs), the patient's own immune cells, with or without prior activation with Phytohemagglutinin (PHA). Prostaglandin E2 (PGE2) is involved in the regulation of different stages of the immune response and different effector mechanisms of immunity. Mesenchymal stromal cells (MSCs) constitutively produce PGE2, and their proliferation is regulated by this prostaglandin through the differential activation of cAMP-dependent protein kinase isoforms. This production of PGE2 is sensitive to the local environment, where inflammatory signals stimulate their induction. During coculture with immune cells, PGE2 production by MSCs is substantially increased and participates in the immunomodulatory effects of MSCs. Moreover, the role of PGE2 in MSC-induced immunosuppressive effects depends on T-cell stimuli, as reported by Rasmusson et al. (Exp Cell Res. 2005 Apr. 15; 305(1):33-41.). PGE2 is effective in the MSC inhibition of T cells activated by phytohaemagglutinin (PHA) rather than by alloantigens. MSCs prevent lymphocyte activation and induce the inhibition of T-cell proliferation through the modulation of COX1/COX2 expression and ultimately PGE2 production.

Cell culturing: Cells are cultured in assay medium (DMEM, low glucose, GlutaMAX™ Supplement, pyruvate (ThermoFisher Scientific, cat no. 21885025)+10% Fetal Bovine Serum, qualified, heat inactivated (ThermoFisher Scientific, cat no. 16140071)) for 3 days in co-culture cell ratio MSC-PBMC 1/5, in presence and absence of PHA (Merck, cat no. 11082132001). The drug product, 40 000 MSCs/well, are seeded per well in 12-well cell culture plates (or 10 000 MSCs/well in 48-well plates). Cell culture plates are incubated at 37° C., 5% $CO_2$ for 2 hours to allow the cells to adhere before PBMCs are added ($2\times10^5$ cells/well in 12-well plates and 50 000 PBMCs/well in 48-well plates) (The seeding of cells is only applicable when the drug product is an adherent cell. If the drug product is exosome or a suspension cell, the PBMC and the drug product are mixed in assay medium).

Assay medium is added to wells without PBMC and assay medium containing 10 μg/ml PHA is added to PBMC containing wells and the cell culture plate is incubated at 37° C., 5% $CO_2$ for 72 hours. The supernatant is removed from each well and centrifuged 5 min 500×g to remove particulates. The supernatant is frozen and stored at −20° C. until further processing for ELISA analysis.

The Parameter™ Prostaglandin E2 Immunoassay kit is used for PGE2 expression detection according to manufacturer's instruction (Bio-Techne, cat no. KGE004B) and is analyzed with Spectramax microplate reader (Molecular Devices, Spectramax 190). The 4PL-algorithm (Four Parameter Logistic Regression) is used to calculate results (software SoftMax Pro 7.0.2, Molecular Devices).

Result

The average expression of PGE2 in pg/ml for drug product is used for relative comparison of patient's own immune cells in with or without of PHA and compared to reference donors. High expression of PGE2 indicates that the drug product is responding to the inflammatory state of the patient's own cells and the higher expression, the more potent is the drug product for this particular patient.

The drug product has been developed to express PGE2 in presence of lymphocytes and the patient's response rate to the drug product is anticipated to correlate with the lymphocyte's ability to take up PGE2. This is measured as a decrease in extracellular PGE2 concentration.

The score is given based on the relative expression caused by the patient's own immune cells in comparison to the reference donors. The score is later used in the Prediction Algorithm (see Example 6).

TABLE 8

Illustrative example of ranking score based on PGE2 expression. Four reference donors are included in the assay and the sample is evaluated in relation to these donors. The references and the sample are scored based on the capacity to induce drug product expression of PGE2 and the reference/sample with the highest expression will score 5, and the lowest (least desirable induction of PGE2 expression) will score 1.

| Donor | PGE2 expression with PHA | Score | Donor | PGE2 expression without PHA | Score |
|---|---|---|---|---|---|
| Ref1 | 9600 | 5 | Ref1 | 3339 | 5 |
| Ref2 | 11400 | 4 | Ref2 | 4202 | 3 |
| Ref3 | 13300 | 3 | Ref3 | 4332 | 2 |
| Ref4 | 14900 | 1 | Ref4 | 5026 | 1 |
| Sample | 14800 | 2 | Sample | 4030 | 4 |

The scoring could also be based on absolute numbers in respect to PGE2 expression as described in Table .

The sample in this example would get the score=2.

TABLE 9

Example of scoring of the sample based on predefined scores for a range of PGE2 expression.

| PGE2 expression range with PHA | Score |
|---|---|
| >15000 | 0 |
| 14999-14000 | 1 |
| 13999-12000 | 2 |
| 11999-10000 | 3 |
| 9999-8000 | 4 |
| <7999 | 5 |

Assay 4-IDO:
Material and Methods:

IDO assay is used to analyze the immunosuppressive capacity of the drug product when the drug product is mesenchymal stem/stroma cells (MSC) based.

The MSC immunomodulatory potential is reported as a measure of indoleamine 2,3-dioxygenase (IDO) activity, determined by measuring tryptophan and kynurenine in the culture supernatant. Indoleamine-pyrrole 2,3-dioxygenase (IDO or INDO EC 1.13.11.52) is a heme-containing enzyme that in humans is encoded by the IDO1 gene. The IDO enzyme converts L-tryptophan to N-formylkynurenine (or kynurenine), an immunosuppressive molecule that acts as an inhibitor of immune cell proliferation, including T cells. The IDO activity is the ratio of kynurenine/tryptophan and can be determined by calculating the amount of tryptophan and kynurenine present in cell culture supernatants using an ELISA kit. When co-cultured with the patient's own immune cells activated by a potent mitogen, mesenchymal stem/stroma cells (MSC) secrete more IDO than when they are unstimulated.

Inducible IDO activity indicates that the patient's own immune cells have the potency to activate the drug product anti-inflammatory response. In other words, the drug product is likely to respond to an inflammation in the patient.

MSC culturing: Seed 10 000 MSC/well in 48-well cell culture plates in 100 µl assay medium (DMEM, low glucose, GlutaMAX™ Supplement, pyruvate (ThermoFisher Scientific, cat no. 21885025)+10% Fetal Bovine Serum, qualified, heat inactivated (ThermoFisher Scientific, cat no. 16140071)). Cell ratio MSC-PBMC 1/5 is used for co-culture both for naïve and activated with PHA (Merck, cat no. 11082132001). Cell culture plate is incubated at 37° C., 5% $CO_2$ for 72 hours. Remove the supernatant from each well and store in micro tubes at −20° C. until further processing for ELISA analysis.

Tryptophan and kynurenine measurements are done according to manuals provided by the ELISA-kit manufacturer (Immundiagnostik AG, cat no. K 3730 and K 3728). Both tryptophan and kynurenine ELISA are performed on the same day but at separate occasions. The two ELISAs are conducted according to manufacturer's instructions; see the manuals for respective ELISA.

Absorption at 450 nm with background subtraction at 620 nm is measured in a Spectramax microplate reader (Molecular Devices, Spectramax 190).

Analyzing results: Amount of absorbance measured is inversely proportional to the amount of amino acid present in the sample; i.e. the lower the OD450 (optical density at 450 nm), the more kynurenine or tryptophan there is. The 4PL-algorithm (Four Parameter Logistic Regression) is used to calculate results (software SoftMax Pro 7.0.2, Molecular Devices), as recommended by kit manufacturer. Concentrations are determined directly from the standard curve. The control samples provided with the kits should are evaluated for acceptability: if outside the acceptable range according to the manufacturer of the kit, the samples need to be re-assayed.

Result

High fold induction of IDO indicates that the drug product is responding to the inflammatory state of the patient's own cells and the higher the fold induction, the more potent is the drug product for this particular patient. The score is given based on the relative fold induction caused by the patient's own immune cells in comparison to the reference donors, shown in Table 10. The score is later used in the Prediction Algorithm (see Example 6).

TABLE 10

Illustrative example of ranking score based on IDO fold increase

| Donor | IDO fold increase | Score |
| --- | --- | --- |
| Ref1 | 150 | 5 |
| Ref2 | 130 | 4 |
| Ref3 | 125 | 3 |
| Ref4 | 114 | 1 |
| Sample | 122 | 2 |

The scoring could also be based on absolute numbers in respect to IDO fold increase as described in Table 11.
The sample in this example would get the score=2.

TABLE 11

Example of scoring of the sample based on predefined scores for a range of IDO fold increase

| IDO fold increase range | Score |
| --- | --- |
| >150 | 5 |
| 149-135 | 4 |

TABLE 11-continued

Example of scoring of the sample based on predefined scores for a range of IDO fold increase

| IDO fold increase range | Score |
| --- | --- |
| 134-125 | 3 |
| 124-120 | 2 |
| 119-110 | 1 |
| <109 | 0 |

Assay 5: Fluorospot
Material and Methods:

The expression of IL-2, IL-4, IL-6, IL-8, IL-12, IL-12/13, IL-13, IL17A IL-21, IL-22, IL-29, IL-31, TGFβ1, GM-CFS, IFNα, IFNγ, apoE and TNFα is analyzed by Fluorospot (MabTech, see Table 12).

Analysis of the patient's own immune cells and/or the drug product. Alternatively, could be of co-culturing or by conditioned media. In the case of the drug product being MSC, seed 10 000 MSC/well in 48-well cell culture plates in 100 µl assay medium (DMEM, low glucose, GlutaMAX™ Supplement, pyruvate (ThermoFisher Scientific, cat no. 21885025)+10% Fetal Bovine Serum, qualified, heat inactivated (ThermoFisher Scientific, cat no. 16140071)). Cell ratio MSC-PBMC 1/5 is used for co-culture both for naïve and activated with PHA (Merck, cat no. 11082132001). Cell culture plate is incubated at 37° C., 5% $CO_2$ for 72 hours.

TABLE 12

Antibodies used in said Fluorospot-assay.

| Fluorospot-assay | Detection antibody |
| --- | --- |
| IL-2 | human mAb MT8G10-biotin, 0.5 mg/ml |
| IL-4 | human mAb IL-4 II-biotin, 1 mg/ml |
| IL-6 | human mAb 39C3-biotin, 1 mg/ml |
| IL-8 | human mAb MT8F19-biotin, 0.5 mg/ml |
| IL-13 | human mAb IL13-3-biotin, 0.5 mg/ml |
| IL-21 | human mAb MT21.3m-biotin, 0.5 mg/ml |
| IL-22 | human mAb MT7B27-biotin, 0.5 mg/ml |
| IL-29 | human mAb MT6G4-biotin, 0.5 mg/ml |
| IL-31 | human mAb MT158-biotin, 0.5 mg/ml |
| IFNα (pan) | human mAbs MT2/4/6-biotin, 1 mg/ml |
| IFNγ | human mAb 7-B6-1-biotin, 1 mg/ml |
| TNFα | human mAb TNF5-biotin, 0.5 mg/ml |
| GM-CSF | human mAb 23B6-biotin, 1 mg/ml |
| TGFβ1 (latent form) | human mAb MT517-biotin, 0.5 mg/ml |

Results

The results are analyzed with the software provided with the Fluorspot reader. The program generates both visual and numeric output.

The patient's own immune cells are scored in relation to the reference donors or by threshold value for positive vs. negative is predefined for each marker. In the case of the drug product being a cell-based drug, also the expression of the drug product in response to co-culturing with the patient's own immune cells can be scored, Table 13

TABLE 13

Marker translation to numeric scores.

| Type of marker | Result | Numeric score | Type of marker | Result | Numeric score |
|---|---|---|---|---|---|
| Positive markers | Negative | 0 | Negative markers | Negative | 0 |
| | Positive | 1 | | Positive | −2 |
| | Higher than reference | 2 | | | |

The scoring of the patient's own immune cells and/or the patient's own immune cells effect on the drug product can be the score from a single marker analysis or a summarized score from multiple markers, each contributing with a sub-score as a score of multiple assays with and/or without stimuli (Table 14).

TABLE 14

Illustrative example of sub-scores for multiple markers, generating a score.

| M1 | M1 S1 | M2 | M3 | M4 S1 | M4 S2 | M4 S3 | Score |
|---|---|---|---|---|---|---|---|
| 1 | 1 | 0 | 0 | 1 | 1 | 1 | 5 |

M1 = marker 1, M2 = marker 2 etc. S1 = stimuli 1, S2 = stimuli 2 etc. M1 and M4 are positive markers. M2 and M3 are negative markers.

The score of the patient's own immune cells is based on the sub-score in comparison with reference donors sub-score for the particular Fluorospot assay. The score is later used in the predictive method as described in Example 6 (see Table 15):

TABLE 15

Illustrative example of sub-scores generating a score from the compiled Fluorospot assays.

| Donor | Sub-score | Score |
|---|---|---|
| Ref1 | 8 | 5 |
| Ref2 | 6 | 3 |
| Ref3 | 7 | 4 |
| Ref4 | 5 | 1 |
| Sample | 6 | 3 |

Furthermore, it is also possible to use some or all of the Fluorospot results as input in the Prediction Algorithm, i.e. data from each analyzed protein as a separate component in the selection algorithm. It is also possible to have different weights of the sub-scores from the Fluorospot assays.

Alternative to using a relative comparison between the sample and reference donors to generate a score is to, directly use the sub-score from the Fluorospot assay in the Prediction Algorithm. The score from the Fluorospot assay of the sample is then divided by the maximum score from the Fluorospot assay possible for the assay and then multiplied by 5. For this example, the score would have been (6/10)*5=3.

Assay 6—Kynurenine:
Material and Methods:
IDO assay is used to analyze the immunosuppressive capacity of the drug product when the drug product is mesenchymal stem/stroma cells (MSC) based. Plasma concentration of kynurenine may be used as a measure of IDO activity.

In order to assess the potential benefit of a MSC treatment, the plasma concentration of kynurenine is measured as a biomarker for immunomodulatory responsive patients. The concentration is measured according to material and methods described in Assay 4.

Analyzing results: Amount of absorbance measured is inversely proportional to the amount of amino acid present in the sample; i.e. the lower the OD450 (optical density at 450 nm), the more kynurenine there is. The 4PL-algorithm (Four Parameter Logistic Regression) is used to calculate results (software SoftMax Pro 7.0.2, Molecular Devices), as recommended by kit manufacturer. Patient plasma is diluted in 1:1 with PBS and the standard is cell culture medium supernatant of a reference batch of the drug product.

Result

High plasma concentration of kynurenine is an indication of a responder and the highest concentration receive the highest score as shown in Table 16. The score is later used in the Prediction Algorithm (see Example 6).

TABLE 16

Illustrative example of ranking score based on plasma concentration of kynurenine (Kyn)

| Donor | Kyn | Kyn score |
|---|---|---|
| Ref1 | 1.87 | 7 |
| Ref2 | 1.61 | 4 |
| Ref3 | 1.23 | 1 |
| Ref4 | 1.85 | 6 |
| Ref5 | 1.40 | 3 |
| Ref6 | 1.24 | 2 |
| Standard | 1.67 | 5 |

The scoring could also be based on absolute numbers in respect to kynurenine concentration as described in Table 17. The standard in this example would get the score=3.

TABLE 17

Example of scoring of the sample based on predefined scores for a range of kynurenine concentration.

| Kynurenine concentration | Score |
|---|---|
| >2 | 5 |
| 2-1.8 | 4 |
| 1.79-1.6 | 3 |
| 1.59-1.4 | 2 |
| 1.39-1.20 | 1 |
| <1.2 | 0 |

Example 5

The present Example describes the analysis of preexisting antibodies with affinity to the drug product. Preexisting antibodies will result in a faster clearing of the drug product in vivo.

Material and Methods:

Serum from the patient is collected and analyzed for HLA antibodies directed towards the drug product. One Lambda (OLI) FlowPRA® Screening (FPRA) Class I and II, LAB-Screen® Mixed (LSMIX) and LABScreen® Single Antigen Class I/II (LSA1/2) bead are used according to manufacturer specifications (Thermo Fisher Scientific Inc.). If a patient is found have preexisting immunization, this analysis will be followed by a secondary analysis for specificity towards the drug product. Followed by for example the FlowDSA- XM™ crossmatch testing with the drug product and/or drug product HLA profile (Thermo Fisher Scientific Inc.).

Results

Results assigned a score value, wherein the highest value is most desirable.

| No HLA-ab detectable | 5 |
| No drug product specific HLA-ab detectable | 3 |
| drug product specific HLA detected | 0 |

Reference donors are not used for scoring purposes but can still be included as standards to validate reproducibility. The desirable result would be to have no detectable antibodies against HLA, followed by HLA response but without specificity towards the drug product.

Example 6

The present Example describes how the results from 2 or more assays are compiled in the Prediction Algorithm Material and Methods The prediction algorithm is an overall assessment of the at least 2 functional and/or potency assays as described in, but not limited to, Example 3, Example 4 and Example 5. Assessment of the assays according to a point system presented in Table 18 below.

Each assay generates a score and the final prediction is based on a total score. The total score may be an additive score as exemplified in Table 18.

TABLE 18

Example of prediction based on additive total score.

| Donor (DX) | IDO | PI | PGE2 | HLA-ab | FluoroS | Total score |
|---|---|---|---|---|---|---|
| Ref1 | 5 | 5 | 5 | 5 | 5 | 25 |
| Ref2 | 4 | 4 | 4 | 5 | 3 | 20 |
| Ref3 | 3 | 2 | 3 | 3 | 4 | 15 |
| Ref4 | 1 | 1 | 1 | 3 | 1 | 7 |
| Sample | 2 | 3 | 2 | 5 | 3 | 15 |

Alternatively, prediction is based on different weights of the assays, thus allowing an assay to be of more or less importance in the prediction as compared to the other assays. An example would be to put a factor two on HLA antibodies and decrease the importance of PGE2 assay to half.

The results from the same examples based on weighed total score are shown in Table 169 (1×[IDO]+1×[PI]+1.5×[PGE2]+2×[HLA-ab]+1×[FluoroS]).

TABLE 16

Example of prediction based on weighted total score

| Donor (DX) | 1 × IDO | 1 × PI | 0.5 × PGE2 | 2 × HLA-ab | 1 × FluoroS | Total score |
|---|---|---|---|---|---|---|
| Ref1 | 5 | 5 | 2.5 | 10 | 5 | 27.5 |
| Ref2 | 4 | 4 | 2 | 10 | 3 | 23 |
| Ref3 | 3 | 2 | 1.5 | 6 | 4 | 16.5 |
| Ref4 | 1 | 1 | 0.5 | 6 | 1 | 9.5 |
| Sample | 2 | 3 | 1 | 10 | 3 | 19 |

Alternatively, the total score can be calculated based on the predefined scoring of each assay as shown in Table , representing a simple additive algorithm (scores achieved from Table 5, Table 7, Table 9, Table 11).

TABLE 20 example of predefined scoring.

| | IDO | PI | PGE2 | HLA-ab | FluoroS | Total score |
|---|---|---|---|---|---|---|
| Sample | 2 | 3 | 2 | 5 | 3 | 20 |

Results

Four reference donors are included in this Example. The intra assay variation of these kinds of assays is usually minor but the inter assay variation is significant. This fact can be handled by addition of reference donors and by making a relative comparison between the patient sample and the reference donors. In a validated setting, the reference donors could be exchanged for a predefined scoring table as described for the respective assay.

The final score of the Prediction Algorithm will generate a prediction of the likelihood of a patient response to the treatment.

In relative measurements, this prediction can be directly linked to in vivo data as exemplified in Table 21.

TABLE 21

Example of prediction of patient response and outcome in vivo.

| Donor (DX) | Total score | Outcome | Prediction |
|---|---|---|---|
| Ref1 | 25 | High response | |
| Ref2 | 20 | Response | |
| Ref3 | 15 | Response | |
| Ref4 | 7 | Low response | |
| Sample | 15 | | Response |

Alternatively, the total score can be directly translated to a prediction as shown in Table 22. Thus, the prediction may be used for recommendation of treatment for the specific patient.

TABLE 17

Example of prediction of total score

| Total score range | Prediction | Recommendation |
|---|---|---|
| >20 | High response | Treatment highly recommended |
| 20-15 | Response | Treatment recommended |
| 14-7 | Low response | Consider treatment |
| <7 | No response | Treatment not recommended |

Example 7

The present example provides a summary of the clinical study design of infusion of the drug product being MSC, into patients diagnosed with type 1 diabetes.

The patient's own immune cells are collected at baseline by collection of blood sample as described in Example 1. The patient's own immune cells are isolated and retrospectively analyzed with the prediction algorithm. Thereby, the present clinical trial is an evaluation of the prediction algorithm. Safety and tolerance as well as changes in beta-cell function, metabolic control and diabetes treatment satisfaction are examined. Any adverse events will be reported and potential causal relationship with drug product will be investigated.

Study design: A combined phase I and phase II study is performed. The first part is an open, dose escalating study consisting of 9 male patients, 18-40 years of age. The second part is a randomized, double-blinded, placebo-controlled, phase I/II study in parallel design comparing treatment with the pooled allogeneic MSC composition as disclosed herein to placebo in adult patients diagnosed with type 1 diabetes. Safety, preservation of endogenous insulin production (measured as C-peptide concentrations) together with metabolic control, diabetes treatment satisfaction and immunological profile are assessed.

A total number of 24 patients are enrolled in the study (9 patients in the first part and 15 patients in the second part) and followed for one year after Final Product/placebo treatment. Inclusion and exclusion criteria are described in Example 8.

In the first part of the study patients 1-3 receive a single dose of 25 million cells, patients 4-6 receive 100 million cells and patients 7-9 receive 200 million cells. The 15 patients in the second part of the study will be allocated with a ratio of 1:1:1 to one of three arms: A. Allogeneic infusion with WJMSCs (batch 1), i.e. Final product batch 1); B. Allogeneic infusion with WJMSCs (batch 2) i.e. Final Product batch 2); and C. placebo infusion. In the statistical analysis group A and B will be pooled and compared with group C. In the second part of the study all patients will receive a fixed single dose of Final Product. A preliminary proposed dose is 100 million MSCs, but no dosing will occur in part 2 before data from part 1 is evaluated to confirm the preliminary proposed dose.

The study starts with a screening period to obtain informed consent, screening, and inclusion to the study. Inclusion to the study must be within two years of type 1 diabetes diagnosis. Throughout the study, all patients will continue their insulin treatment, with insulin doses adjusted to maintain optimal blood glucose control as per clinical practice. All patients, 1-24, will follow the set visit schedule and during each visit a set of tests and procedures will take place according to Table 23.

TABLE 18

Overview of study. Visits 3 and 4 may be performed +/− 3 days, visit 5 may be performed +/− 7 days and 6-8 may be performed +/− 14 days from day indicated above.

|  | Screening visit | Baseline visit | Treatment | | | Follow up | | |
|---|---|---|---|---|---|---|---|---|
|  |  |  | Visit number | | | | | |
|  | 1 | 2 | 3 | 4 | 5 | 6 | 7 | 8 |
| Days | −14-0 | 0 | 7 | 37 | 97 | 187 | 277 | 372 |
| Informed consent | X | | | | | | | |
| Eligibility criteria | X | | | | | | | |
| Demography | X | | | | | | | |
| Medical history | X | | | | | | | |
| Concomitant medications | X | X | X | X | X | X | X | X |
| Baseline symptoms | X | X | | | | | | |
| Adverse events | | X | X | X | X | X | X | X |
| Optimizing diabetes care | X | X | X | X | X | X | X | X |
| Randomization | | X | | | | | | |
| Insulin requirement | | X | | | | X | | X |
| MMTT | | X | | | | | | X |
| CGM | | X | | | | | | X |
| WJMSC/placebo infusion | | | X | | | | | |
| DTSQ | | X | | | | | | X |
| Immunology tests | | X | | X | X | X | | X |
| Clinical chemistry | X | X | | X | X | | | X |
| HLA class I genotype | | X | | | | | | |
| HbA1c | X | X | | X | X | X | X | X |
| Pregnancy test/ HCG) | X | | | | | | | |
| Vital signs (heart rate, blood pressure) | X | X | X | X | X | X | X | X |
| Dispensing diary card | | X | X | X | X | X | X | |
| Collecting diary card | | | X | X | X | X | X | X |

The end of study is defined as the last participant's last follow up.

Throughout the study, patient safety is of importance. Each serious adverse effect (SAE) that is at least possibly related to the Final Product is to be classified by the investigator as expected or unexpected and followed up according to protocol.

Results

Clear insights into the medical situation of the 24 included patients. This includes safety and adverse events parameters and will allow to gain insights into the set efficacy endpoints.

No or only minor side effects of MSC treatment have previously been observed in clinical studies for a number of diseases such as graft versus host disease, tissue regeneration after myocardial infarct or liver cirrhosis, or in osteogenesis imperfecta. No increased risk of tumor development in patients is known, and no ectopic tissue formation has been observed (von Bahr et al., (2012) Biol Blood Marrow Transplant; 18: 557-564, von Bahr L et al., (2012). Stem Cells; 30: 1575-1578). Similarly, in first studies in adult patients newly diagnosed for type 1 diabetes no side effects were observed (Hu J et al., (2013). Endocr J; 60: 347-357, Carlsson P O et al., (2015) Diabetes. 2015; 64(2):587-92).

WJMSC from the manufacturer used for the present study have previously been used in hospital exemption procedures for various conditions and the safety profile of the cells is consistent and well tolerated with only mild and transient adverse reactions related to the product. However, serious adverse events and deaths has been reported, caused by the underlying disease, for instant terminal ALS patients and patients suffering grade 4 GVHD, receiving therapy. In the present study, any expected adverse events are mild and transient flu-like symptoms.

The present inventive treatment with the Final product, which comprises the drug product, is an allogeneic transplantation of cells from multiple donors and HLA mismatch is guaranteed. There is a theoretical risk of HLA immunization of the patients that might be devastating if the T1DM patient later in life is in need of a kidney transplantation.

Antibodies against foreign HLA without clinical relevance is expected in up to 20% of the patients.

A successful intervention would be highly beneficial for subjected patients likely providing them with a lower HbA1c, less blood glucose fluctuations, and diminished risk of ketoacidosis. It would also substantially decrease the risks of severe hypoglycemic events and late complications. The decrease in C-peptide concentration pre-treatment and 12-month post treatment is expected to be less for patients receiving the inventive Final Product as compared to patients receiving placebo (control).

The evaluation of the prediction algorithm is focused on how the patient outcome correlates with the predicted outcome. Patients that are responders to the drug product and show the highest benefit of therapy in terms of increase in delta c-peptide (or smallest decrease) are expected to have the most desirable scores in the predictive algorithm.

Example 8

The present example describes the selection criteria for the study population. Each patient enrolled in the study has to fulfill all inclusion criteria and none of the exclusion criteria.

Inclusion and Exclusion criteria: Subjects will be recruited from the population of newly diagnosed type 1 diabetes patients.

Patients eligible for inclusion in this study must fulfill the following criteria: 1. Given written informed consent for participation of the study; 2. Clinical history compatible with type 1 diabetes diagnosed less than 2 years before enrollment; 3. In the first part of the study patients 1-9 only male patients between 18-40 years of age will be included. In the second part of the study, patients 10-24, both male and female patients 18 to 40 years of age (inclusive at both ends) will be included; 4. Fasting plasma C-peptide concentration >0.12 nmol/L; and 5. Nonpregnant women and using approved method of contraception/abstinence.

Patients fulfilling any of the following criteria at screening are not eligible for inclusion in this study: 1. Inability to provide informed consent; 2. patients with body mass index (BMI) >30, or weight >100 kg; 3. patients with weight <50 kg; 4. patients with unstable cardiovascular status incl. NYHA class III/IV or symptoms of angina pectoris, uncontrolled hypertension (≥60/105 mmHg), active on-going infections, tuberculosis, or at risk of tuberculosis or mycosis, HIV, Treponema pallidum, hepatitis B antigen or hepatitis C, demyelinating disease, proliferative retinopathy and previous or known malignancy; 5. patients with any immune suppressive treatment; 6. Pregnant or lactating women; 7. Taking oral anti-diabetic therapies or any other concomitant medication which may interfere with glucose regulation other than insulin; 8. patients with GFR<80 ml/min/1.73 m2 body surface; 9. patients with known hypersensitivity against any excipients, i.e. dimethyl sulfoxide (DMSO).

Results

Study population of 24 individuals is selected based on the criteria described above.

Example 9

The present Example describes how the clinical study outcome relates to the predictive algorithm conducted with the patient's own immune cells.

Material and Methods:

The patient's own immune cells have been isolated from a peripheral blood sample collected at base line. The cells are isolated and cultured as described above and are then used in the assays used in the Prediction Algorithm.

Results

The score from the Prediction Algorithm is compared to the clinical effect of the drug product, i.e. delta c-peptide at baseline and after 12-month post treatment. The patients having the greatest benefit of treatment as determined by least reduction in c-peptide or increase in c-peptide over time, are anticipated to have the highest score in the prediction algorithm. It is expected that a correlation between outcome of treatment and prediction will be observed. Hence, it is expected that the prediction method as disclosed herein, may be used to predict the treatment outcome of future drug product treatment on an individual patient level.

Example 10

The present Example describes how the preclinical study of renal transplant is conducted in an animal model.

Material and methods

Blood samples from the animals are collected and PBMC is isolated as described in Example 1. Functional/potency assays are performed with the drug product to generate a score using the predictive algorithm described in Example 11 and subsequently in Example 6.

After that, the animals will go through a renal transplant and also receive drug product treatment. Further treatment might be given to induce transplant rejection. Transplant outcome is measured based on engraftment and inflammatory status of the animal at different time point.

Results

Transplanted animals are expected to have similar but not identical benefit of the drug product therapy. The extreme cases are transplant related death, transplant rejection in contrast to engraftment of the transplant with mild or no side effects. Mortality and transplant rejection should correspond to a poor predictive total score and engraftment with low or no side effects should correspond to a high predictive total score, for a desirable outcome, i.e. supporting the predictive algorithm.

Example 11

The present Example describes how the preclinical study outcome relates to the predictive algorithm conducted with the model animal's own immune cells.

Material and Methods

The functional/potency assays are conducted with the animal's own immune cells from PBMC. The results from the assays are used in the predictive algorithm to generate a predictive score.

The predictive score is compared to the transplant outcome.

Results

The animals with engraftment and only mild side effects are expected to have the highest prediction score, whereas the animals that died or experienced transplant rejection are expected to have the lowest prediction scores.

Example 12

The present Example describes how the prediction algorithm corresponds to measured outcome in ALS model animals treated with drug product.

Material and Methods

The transgenic mouse model, SOD1-G93A, expresses large amounts of mutant SOD1, and develops adult-onset neurodegeneration of spinal motor neurons and progressive motor deficits leading to paralysis.

Brian biopsies will be used for isolation of the microglia and the drug product's potential to convert the microglia into an anti-inflammatory state will be evaluated on an individual level as described in example 3. The microglia cells could also be co-cultured with the drug product to investigate the microglia cells effect on the drug Product in the case of the drug product being cells, typically MSC.

Furthermore, a blood sample will be collected to analyze PBMC interaction with the drug product.

The results from the functional/potency assays described in Example 3, Example 4 and Example 5 are entered into the prediction algorithm to generate a predicative score. The model animals are transplanted with the study drug and evaluated based on the drug product effect to slow down or revert disease progression and/or by measuring cytokine and signaling molecules indicating inflammatory status.

Results

The scope is to evaluate the correlation between the predictive impact of therapy with measured impact presented in Example 13

Example 13

The present Example describes how the preclinical study outcome relates to the predictive algorithm conducted with the model rodent's own immune cells.

Material and Methods

Predictive algorithm based on 2 or more functional/potency assays. The results from the functional/potency assays are entered and an individual predictive score is calculated.

The score should be in relation to the effect of the drug product therapy, when comparing the individuals in Example 12.

Results

Subjects having the highest predictive scores as evaluated by the prediction algorithm are anticipated to experience the greatest benefit of the drug product therapy and vice versa.

Example 14

The present Example describes how the clinical study outcome relates to the predictive algorithm conducted with the patient's own immune cells. The score from the Prediction Algorithm were compared to the clinical effect of the drug product by measuring the change in concentration of glycated haemoglobin (HbA1c) before treatment in comparison with 1 and 3 months (and 6 months for as subset of patients) after treatment. HbA1c gives an overall picture of the average blood sugar levels have been over a period of weeks. The patients having the greatest benefit of treatment as determined by higher reduction in HbA1c, are anticipated to have the highest score in the prediction algorithm.

Material and Methods:

The patient's own immune cells have been isolated from a peripheral blood sample collected at base line. The cells were isolated and cultured as described in Example 1. The proliferation assay and prostaglandin assay were done as described in Assay 1 (Example 3) and Assay 3 (Example 4) and the results obtained are then used in the Prediction Algorithm.

Results

The results from Assay 1 and Assay 3 are presented in Tables 24 and 25 below.

TABLE 24

Results from the Proliferation assay (PI).

| Patient | PI with PHA | PI with PHA and CB1 | Delta PI |
|---|---|---|---|
| Pat1 | 2.17 | 1.58 | −0.59 |
| Pat2 | 2.21 | 1.78 | −0.44 |
| Pat3 | 2.11 | 1.73 | −0.38 |
| Pat4 | 2.55 | 1.66 | −0.89 |
| Pat5 | 3.49 | 1.91 | −1.58 |
| Pat6 | 1.69 | 1.33 | −0.36 |
| Reference | 2.10 | 1.38 | −0.72 |

TABLE 25

Results from the Prostaglandin E2 assay

| Patient | Relative PGE2 |
|---|---|
| Pat1 | 0.71 |
| Pat2 | 0.92 |
| Pat3 | 0.95 |
| Pat4 | 1.09 |
| Pat5 | 0.63 |
| Pat6 | 1.23 |
| Reference | 1.00 |

A relative PGE2 was used to decrease the effect of interassay variation. Reference samples were included in every experiment and used a as a relative expression with an assigned value of 1. PGE2 concentration in presence of patient's own cells are divided by the concentration of the reference sample. A value over 1 indicates increased concentration and under 1 decreased concentration relative to the reference sample.

Prediction algorithm

The patient cells having the highest change in proliferation index was scored with 7, the second highest with 6 and so on.

The patient cells having the lowest relative extracellular concentration of prostaglandin was scored with 7, the second lowest with 6 and so on.

The weight of PI is 1 and for PGE2 it is 2, i.e. the total score was calculated as 1×(PI score)+2×(PGE2 score)=Total Score.

A reference sample was used as threshold value and patients with a total score higher than the reference sample were predicted to be responders, lower than the reference sample were predicted to not respond to treatment.

TABLE 26

Summary of prediction.

| Patient | Delta PI | Relative PGE2 | PI score | PGE2 score | Total Score | Prediction outcome |
|---|---|---|---|---|---|---|
| Pat1 | −0.59 | 0.71 | 4 | 6 | 16 | Responder |
| Pat2 | −0.44 | 0.92 | 3 | 5 | 13 | Responder |
| Pat3 | −0.38 | 0.95 | 2 | 4 | 10 | Not responder |
| Pat4 | −0.89 | 1.09 | 6 | 2 | 10 | Not responder |
| Pat5 | −1.58 | 0.63 | 7 | 7 | 21 | High responder |
| Pat6 | −0.36 | 1.23 | 1 | 1 | 3 | Not responder |
| Reference | −0.72 | 1.00 | 5 | 3 | 11 | Threshold reference |

The predicted response was compared with clinical data from 6 patients. HbA1c concentration in blood was measured before treatment and compared with concentration 1 and 3 months after treatment. Response is determined as decrease in HbA1c concentration.

TABLE 27

Summary of clinical data.

|  |  | Pat1 | Pat2 | Pat3 | Pat4 | Pat5 | Pat6 |
|---|---|---|---|---|---|---|---|
| HBA1c | Screen | 47 | 41 | 37 | 34 | 60 | 38 |
| mmol/mol | Baseline | 46 | 42 | 37 | 35 | 57 | — |
|  | 1 month | 41 | 39 | 36 | 34 | 47 | 38 |
|  | 3 months | 44 | 40 | 40 | 37 | 53 | 39 |
|  | 6 months | 47 | 41 | 43 | — | — | — |

An average of HbA1c at screening and baseline was used as concentration before treatment, i.e. an average of HbA1c 14 days and approximately 7 days before treatment. 1 month and 3 month are single measurements 30 and 90 days after the treatment, respectively.

The patient predicted to have the highest response (total score 21) also showed the largest decrease in HbA1c. All three patients predicted to respond had a decrease in HbA1c levels observed for at least 3 months whereas the patients with total score below the threshold reference showed no significant decrease at 1 month and no or even decrease in HbA1c at 3 months. Thus, the present prediction algorithm successfully predicts which patients will respond, highly respond or not respond to treatment with the drug product.

Example 15

In the present Example, an additional assay is added to analysis and prediction described in Example 14 and the clinical study outcome is related to the predictive algorithm conducted with the patient's own immune cells. As described in Example 14, the score from the Prediction Algorithm is compared to the clinical effect of the drug product by measuring the change in concentration of glycated haemoglobin (HbA1c).

The patients having the greatest benefit of treatment as determined by higher reduction in HbA1c, are anticipated to have the highest score in the prediction algorithm.

Material and Methods:

The patient's own immune cells have been isolated from a peripheral blood sample collected at base line. The cells were isolated and cultured as described in Example 1. The results from the of kynurenin assay is used as an indicator for the activity of Indolamine-2,3-Dioxygenase (IDO) and was performed as described in Assay 6 (Example 4). The results obtained are then used in the Prediction Algorithm.

TABLE 28

Plasma concentration of kynuinine and score for patients 1-6.

|  | Kynurinine concentration | Kyn score |
|---|---|---|
| Pat1 | 1.87 | 7 |
| Pat2 | 1.61 | 4 |
| Pat3 | 1.23 | 1 |
| Pat4 | 1.85 | 6 |
| Pat5 | 1.40 | 3 |
| Pat6 | 1.24 | 2 |
| Reference | 1.67 | 5 |

Prediction Algorithm

The patient cells having the highest change in proliferation index was scored with 7, the second highest with 6 and so on.

The patient cells having the lowest relative extracellular concentration of prostaglandin was scored with 7, the second lowest with 6 and so on.

The patient with the highest plasma concentration of kynurenine was scored with 7, the second highest with 6 and so on.

The weight of PI is 1 and for PGE2 it is 2 and for kynurenine is 1, i.e. the total score was calculated as 1×(PI score)+2×(PGE2 score)+1×(Kyn)=Total Score.

A reference sample was used as threshold value and patients with a total score higher than the reference samples were predicted to be responders and patients with a total score lower than or the same as the reference sample were predicted to not respond to treatment.

The predicted response was compared with clinical data from 6 patients (as shown in Table 29). HbA1c concentration in blood was measured before treatment and compared with concentration 1 and 3 months after treatment. Response is determined as decrease in HbA1c concentration.

TABLE 29

Summary of prediction (including the kynuinine assay).

| | Delta PI | Relative PGE2 | Kyn | PI score | PGE2 score | Kyn score | Total Score | Prediction outcome |
|---|---|---|---|---|---|---|---|---|
| Pat1 | −0.59 | 0.71 | 1.87 | 3 | 6 | 7 | 22 | Responder |
| Pat2 | −1.24 | 0.92 | 1.61 | 6 | 5 | 4 | 20 | Responder |
| Pat3 | −0.38 | 0.95 | 1.23 | 2 | 4 | 1 | 11 | Not responder |

TABLE 29-continued

Summary of prediction (including the kynuinine assay).

| | Delta PI | Relative PGE2 | Kyn | PI score | PGE2 score | Kyn score | Total Score | Prediction outcome |
|---|---|---|---|---|---|---|---|---|
| Pat4 | −0.89 | 1.09 | 1.85 | 5 | 2 | 6 | 15 | Not responder |
| Pat5 | −1.58 | 0.63 | 1.40 | 7 | 7 | 3 | 24 | High responder |
| Pat6 | −0.36 | 1.23 | 1.24 | 1 | 1 | 2 | 5 | Not responder |
| Reference | −0.72 | 1.00 | 1.67 | 4 | 3 | 5 | 15 | Threshold reference |

An average of HbA1c at screening and baseline was used as concentration before treatment, i.e. an average of HbA1c 14 days and approximately 7 days before treatment.

1 month and 3 month are single measurements 30 and 90 days after the treatment, respectively.

The patient predicted to have the highest response (total score 24) also showed the largest decrease in HbA1c (from 60-53 HBA1c mmol/mol). All three patients (patient 1, 2 and 5) predicted to respond had a decrease in HbA1c levels observed for at least 3 months. Patients 1, 2 and 5 all show total score values of at least 20, whereas the patients with total score below or at the threshold reference of 15 showed no significant decrease at 1 month and no or even decrease in HbA1c at 3 months (patient 3, 4 ad 6). The addition of the kynurenin assay to the prediction assay further improved the differentiation of responder from non-responder patients.

Itemized List of Embodiments

1. A method for in vitro prediction of the in vivo efficacy in a patient of treatment with a drug product based on an overall assessment comprising the step of evaluating at least properties a) and b) or at least properties b) and c) by at least 2 assays, wherein said properties are:
   a) The in vitro reaction of said patient's own immune cells when exposed to the drug product;
   b) The reaction of said drug product when exposed to said patient's own immune cells; and
   c) Any preexisting antibodies in said patient, which antibodies exhibit affinity for said drug product.
2. Method for in vitro prediction according to item 1, wherein said step of evaluating at least said properties comprises evaluating all three properties a), b) and c).
3. Method for in vitro prediction according to item 1 or 2, wherein said at least two assays are functional and/or potency assays.
4. Method for in vitro prediction according to any one of items 1-3, wherein said drug product is selected from the group consisting of whole cells, live cells, dead cells, lyophilized cells, extracellular vesicles obtained from cell culture, and exosomes; such as the group consisting of mesenchymal stem cells (MSCs), exosomes from MSCs and vesicles from MSCs.
5. Method for in vitro prediction according to any one of items 1-4, wherein said drug product is or comprises live cells, such as live MSCs, such as isolated live cells, such as isolated live MSCs.
6. Method for in vitro prediction according to any one of items 1-5, wherein said MSCs are an allogeneic MSC population, such as an isolated allogeneic MSC population, such as a pooled allogeneic MSC population, such as an isolated pooled allogeneic MSC population.
7. Method for in vitro prediction according to item 6, wherein said allogeneic MSC population comprises cells derived from at least 1, such as at least 2, such as at least 3, such as at least 4, such as at least 5, such as at least 6, such as at least 7, such as at least 8, such as at least 9, such as at least 10 individual donor(s).
8. Method for in vitro prediction according to any one of items 6-7, wherein said allogeneic MSC population is an isolated pooled allogenic population, wherein the number of cells derived from any one donor does not exceed 50% of the total cell number.
9. Method for in vitro prediction according to any one of items 6-8, wherein said allogenic MSC population have at most been subject to seven passages, such as at most six passages, such as at most five passages, such as at most four passages, such as at most three passages, such as one, two or three passages.
10. Method for in vitro prediction according to any one of items 6-9, wherein said allogenic MSC population has been subject to 2-6, such as 2-5, such as 2-4, such as 2-3 passages.
11. Method for in vitro prediction according to any one of items 4-10, wherein said MSCs are selected from the group consisting of bone marrow derived MSCs, peripheral blood derived MSCs, adipose tissue derived MSCs, dental tissue derived MSCs, placenta derived MSCs, umbilical cord derived MSCs, amniotic fluid derived MSC, cord blood derived MSCs, Wharton Jelly derived MSCs, decidua derived MSCs, chondrion membrane derived MSCs and amnion membrane derived MSCs.
12. Method for in vitro prediction according to any one of items 1-11, wherein said patient's own immune cells are selected from the group consisting of peripheral blood monocyte cells (PBMC); T lymphocytes from peripheral blood; T lymphocytes from the central nervous system (CNS); and microglia cells from the CNS, such as the group consisting of PBMC and microglia.
13. Method for in vitro prediction according to any one of items 1-12, wherein at least 2 assays are least 3 assays, such as at least 4 assays, such as at least 5 assays, such as at least 6 assays or more.
14. Method for in vitro prediction according to any one of items 1-13, wherein evaluation of property a) and/or b) comprises co-cultivation of the patient's own immune cells with the drug product.
15. Method for in vitro prediction according to any one of items 1-14, wherein evaluation of property a) comprises evaluation of protein expression of the patient's own immune cells when the patient's own immune cells are co-cultivated with the drug product.
16. Method for in vitro prediction according to any one of items 1-15, wherein property a) is evaluated with or without stimuli.
17. Method for in vitro prediction according to any one of items 1-16, wherein said evaluation of protein expression in property a) is the evaluation of the expression at least one of the markers selected from the group consisting of CD11b, CD14, CD68 and CD200r, such as evaluation of the expression of at least of CD14.
18. Method for in vitro prediction according to item 17, wherein a change in the expression of any one of markers selected from the group consisting of CD11b, CD14, CD68 and CD200r is indicative of favorable response of patient's own immune cells to said drug product.

19. Method for in vitro prediction according to any one of items 1-18, wherein evaluation of property b) comprises evaluation of protein expression of the drug product when the drug product is co-cultivated with patient's own immune cells.

20. Method for in vitro prediction according to any one of items 1-19, wherein for property b) said at least 2 functional and/or potency assays evaluate at least one of alterations in proliferation; protein expression; protein excretion; and cell marker expression.

21. Method for in vitro prediction according to any one of items 1-20, wherein property b) is evaluated with or without stimuli.

22. Method for in vitro prediction according to any one of items 1-21, wherein said at least 2 assays comprise at least one assay measuring the immunosuppressive capacity of said drug product in property a) and/or b).

23. Method for in vitro prediction according to item 22, wherein said at least one assay measuring the immunosuppressive capacity of said drug product measures indoleamine-2,3-dioxygensase (IDO) activity in property b).

24. Method for in vitro prediction according to any one of items 22-23, wherein said at least one assay measuring the immunosuppressive capacity of said drug product measures the effect of said drug product on the proliferation of peripheral blood mononuclear cells (PBMCs) in property a).

25. Method for in vitro prediction according to item 24, wherein said proliferation of PBMCs is the proliferation of T-lymphocytes, such as the proliferation of phytohaemagglutinin (PHA) stimulated T-lymphocytes.

26. Method for in vitro prediction according to any one of items 1-25, wherein said at least 2 assays comprise at least one assay measuring prostaglandin E2 secreted by said drug product in property b).

27. Method for in vitro prediction according to item 26, wherein said at least one assay measuring prostaglandin E2 secreted by said drug product comprises measuring prostaglandin E2 secreted by said drug product when co-cultured with PBMCs, such as PHA stimulated PBMCs, such as PHA stimulated T-lymphocytes.

28. Method for in vitro prediction according to any one of items 1-27, wherein said at least 2 assays comprise at least one assay measuring HLA-G expression in said drug product in response to IFNγ, IL-10 and/or PHA in property b).

29. Method for in vitro prediction according to any one of items 1-28, wherein said at least 2 assay comprise at least one assay measuring the protein expression and/or cytokine expression of the patient's own immune cells in property a) and/or of the drug product in property b).

30. Method for in vitro prediction according to item 29, wherein said at least one assay measuring the protein expression and/or cytokine expression measures the expression of one or several proteins or cytokines selected from the group consisting of IL-2, IL-4, IL-6, IL-8, IL-12, IL-12/13, IL-13, IL17A, IL-21, IL-22, IL-29, IL-31, TGFβ, VEGF, FGF, GM-CFS, IFNα, IFNγ, apo E and TNFα; such as the group consisting of IL-6, IL-8, GM-CSF and TGFβ; such as the group consisting of at least IL-6.

31. Method for in vitro prediction according to item 30, wherein the expression of at least 2, such as at least 3, such as at least 4, such as at least 5, such as at least 6, such as at least 7, such as at least 8, such as at least 9, such as at least 10, such as at least 11, such as at least 12, such as at least 13, such as at least 14, such as at least 15, such as at least 16, such as at least 17, such as at least 18, such as all 19 of said proteins and/or cytokines is measured as defined in item 30.

32. Method for in vitro prediction according to any one of items 29-31, wherein said expression is measured in absence and/or presence of at least one stimuli.

33. Method for in vitro prediction according to item 32 wherein said stimuli is an immune response modifying stimuli.

34. Method for in vitro prediction according to item 33, wherein said immune response modifying stimuli is selected from the group consisting of PBMCs, stimulated PBMCs, such as PBMCs stimulated with PHA, IL10, gamma-aminobutyric acid (GABA) and interferon gamma (IFNγ).

35. Method for in vitro prediction according to item 33 or 34 wherein said immune response modifying stimuli is gamma-aminobutyric acid (GABA).

36. Method for in vitro prediction according to item 33 or 34, wherein said immune response modifying stimuli is a cytokine, such as interferon gamma (IFNγ).

37. Method for in vitro prediction according to item 33, wherein immune response modifying stimuli is selected from the group consisting of polyinosinic:polycytidylic acid (Poly I:C), resiquimod (r848), gamma-aminobutyric acid (GABA) and IFNγ, such as the group consisting of Poly I:C and IFNγ.

38. Method for in vitro prediction according to any one of items 32-34, wherein said stimuli is PBMCs, such as stimulated or unstimulated PBMCs, such as PHA stimulated PBMCs, such as PHA stimulated T-lymphocytes.

39. Method for in vitro prediction according to any one of items 1-38, wherein an inflamed state is predicted to be reverted if the results in a) and/or b) show at least one of 1) a decrease of proinflammatory immune cells proliferation; 2) a decrease in secretion of proinflammatory molecules; 3) switching of immune cells from a proinflammatory to an anti-inflammatory phenotype; 4) apoptosis of CD8+ T cells; 5) apoptosis of memory B cells; and 6) apoptosis of memory T cells; such as wherein an inflamed state is predicted to be reverted if the results in a) and/or b) show at least one of 1) a decrease of proinflammatory immune cells proliferation; 2) a decrease in secretion of proinflammatory molecules; and 3) switching of immune cells from a proinflammatory to an anti-inflammatory phenotype.

40. Method for in vitro prediction according to any one of items 1-39, wherein in property c) serum from the patient is analyzed for the presence of HLA antibodies; such as HLA antibodies without specific affinity for the drug product and HLA antibodies with specific affinity for the drug product.

41. Method for in vitro prediction according to item 40, wherein no presence of HLA antibodies is the most desirable result and the presence of HLA antibodies with specific affinity for the drug product is the least desirable result.

42. Method for in vitro prediction according to any one of items 1-41, wherein an individual score value is assigned to the results of each functional and/or potency assay evaluating at least one of properties a), b) and c) and wherein said the overall assessment comprises allocating a total score value of the in vitro prediction and wherein the total score value is an additive total score value or a weighed total score value.
43. Method for in vitro prediction according to item 42, wherein the individual score value is assigned based on a comparison of the assay result to at least one reference result.
44. Method for in vitro prediction according to item 42, wherein the individual score value is assigned based on a comparison of the assay result to an absolute value.
45. Method for in vitro prediction according to any one of items 42-44, wherein in the case of a higher individual score value being indicative of more desirable assay result, a higher total score value is indicative of in vitro prediction of desirable in vivo efficacy; or wherein in the case of a lower individual score value being indicative of more desirable assay result, a lower total score value is indicative of in vitro prediction of desirable in vivo efficacy.
46. Method for in vitro prediction according to any one of items 42-45, wherein said in vitro prediction predicts if an immunological reaction will occur in said patient to said drug product; or wherein said in vitro prediction predicts the likelihood of an undesirable immunological reaction in said patient to said drug product.
47. Method for in vitro prediction according to any one of items 42-46, wherein said in vitro prediction predicts if a therapeutically desirable response will occur in said patient to treatment with said drug product or wherein said in vitro prediction predicts the likelihood of therapeutically desirable response in said patient of treatment with said drug product.
48. Method for in vitro prediction according to any one of items 42-47, wherein said in vitro prediction predicts if the patient will exhibit a high response, a response, a low response or no response to treatment with said drug product or wherein said in vitro prediction predicts if the patient will exhibit a response or no response to treatment with said drug product.
49. Method for in vitro prediction according to any one of items 42-48, wherein said additive total score value is obtained by addition of individual score values for each assay.
50. Method for in vitro prediction according to any one of items 42-48, wherein said total score value is a weighed total score value obtained by 1) assigning a weight to the individual score value for each assay and 2) adding the weighed individual score values to obtain a weighed total score value.
51. Method for in vitro prediction according to any one items 1-50, wherein said patient suffers from a disorder which may be subject to treatment with the drug product.
52. Method for in vitro prediction according to item 51, wherein said disorder is selected from the group consisting of autoimmune disorders, inflammatory disorders and transplantation associated complications; such as the group consisting of autoimmune diabetes, amyotrophic lateral sclerosis and renal transplantation associated complications.
53. Method of treatment of a patient in need thereof, wherein said patient is treated with a drug product if said drug product is predicted to be efficacious in vivo based on the method for in vitro prediction of said in vivo efficacy as defined in any one of items 1-52.
54. Method of treatment according to item 53, wherein said patient is in need of immunosuppressive treatment.
55. Method of treatment according to item 53 or 54, wherein said patient is suffering or is at risk of suffering from a disorder selected from autoimmune disorders, inflammatory disorders and transplantation associated complications, such as autoimmune diabetes, amyotrophic lateral sclerosis or renal transplantation associated complications.
56. Method of treatment according to any one of items 53-55, wherein said patient is an animal, such as a mammal, such as a human.
57. In vitro use of a drug product for the in vitro prediction of the efficacy of said drug product in vivo, wherein said prediction is according to the method for in vitro prediction of in vivo efficacy as defined in any one of items 1-52.
58. In vitro use according item 57, wherein said drug product is selected from the group consisting of whole cells, live cells, dead cells, lyophilized cells, extracellular vesicles obtained from cell culture, and exosomes; such as the group consisting of MSCs, exosomes from MSCs, and vesicles from MSCs.
59. In vitro use according to item 58, wherein said drug product is live cells, such as live MSCs, such as isolated live cells, such as isolated live MSCs.
60. In vitro use according to item 58 or 59, wherein said MSCs are an allogeneic MSC population, such as an isolated allogeneic MSC population, such as a pooled allogeneic MSC population, such as an isolated pooled allogeneic MSC population.
61. In vitro use according to any one of items 57-60, for making a patient specific treatment decision.
62. In vitro use according to item 61, wherein said patient is in need of immunosuppressive treatment.
63. In vitro use according to any one of items 61-62, wherein said patient is suffering or at risk of suffering from a disorder selected from autoimmune disorders, inflammatory disorders and transplantation associated complications.
64. In vitro use according to item 63, wherein said disorder is autoimmune diabetes.
65. In vitro use according to item 63, wherein said disorder is amyotrophic lateral sclerosis.
66. In vitro use according to item 63, wherein said disorder is renal transplantation associated complications.
67. A system for predicting the efficacy of a drug product prior to treatment of a patient in need thereof with said drug product, comprising the drug product and a total score based on results from at least 2 assays where the patient's own immune cells have been exposed in vitro to said drug product and wherein said prediction comprises the method as defined in any one of items 1-52.
68. System according to item 67, wherein said drug product is selected from the group consisting of whole cells, such as live cells, dead cells, or lyophilized cells; extracellular vesicles obtained from cell culture; exosomes; and conditioned media, such as the group consisting of MSCs, exosomes from MSCs, vesicles from MSCs and conditioned culture media from MSC culture.
69. System according to any one of items 67-68, wherein said drug product is an allogeneic MSC population as defined in any one of items 5-11.
70. System according to any one of items 67-69, wherein said prediction comprises the method as defined in any one of items 42-52.

71. Drug product for use in treatment and/or prevention of a disorder, wherein the drug product is predicted to be efficacious in vivo based on the method for in vitro prediction of said in vivo efficacy as defined in any one of items 1-52.

72. Drug product for use according to item 71, wherein said disorder is selected from the group consisting of autoimmune disorders, inflammatory disorders and transplantation associated complications; such as the group consisting of autoimmune diabetes, amyotrophic lateral sclerosis and renal transplantation associated complications.

73. Drug product for use according to any one of items 71-72, wherein said drug product is selected from the group consisting of whole cells, live cells, dead cells, lyophilized cells, extracellular vesicles obtained from cell culture, and exosomes; such as the group consisting of MSCs, exosomes from MSCs and vesicles from MSCs.

74. Drug product for use according to any one of items 71-73, wherein said drug product is an allogeneic MSC population as defined in any one of items 5-11.

The invention claimed is:

1. A method of treating a patient in need thereof for a disorder selected from the group consisting of autoimmune disorders, inflammatory disorders, and transplantation associated complications, comprising:
  evaluating in vitro the in vivo efficacy in a patient of treatment with a drug product, comprising:
    measuring at least properties (a) and (b) or at least properties (b) and (c) by at least two assays, wherein the properties are:
      (a) the in vitro reaction of said patient's own immune cells when exposed to the drug product;
      (b) the reaction of said drug product when exposed to said patient's own immune cells; and
      (c) any preexisting antibodies in said patient, which antibodies exhibit affinity for said drug product, wherein for property (c) serum from the patient is analyzed for the presence of anti-HLA antibodies with specific affinity for the drug product;
  determining the product as efficacious based on at least properties (a) and (b) or at least properties (b) and (c) if the results in (a) and/or (b) show at least two of:
    1) a decrease of proinflammatory immune cells proliferation;
    2) a decrease in secretion of proinflammatory molecules;
    3) switching of immune cells from a proinflammatory to an anti-inflammatory phenotype;
    4) apoptosis of CD8+ T cells;
    5) apoptosis of memory B cells; and
    6) apoptosis of memory T cells;
  and/or if the results in (c) show (i) no anti-HLA antibodies are detected or (ii) anti-HLA antibodies with no specific affinity for HLA are detected, wherein no specific affinity refers to a $K_D$ value of $10^{-4}$ M or lower affinity; and
  administering the drug product to the patient to treat the autoimmune disorder, inflammatory disorder, or transplantation associated complication;
  or otherwise determining the drug product as inefficacious and withholding the drug product from the patient;
  wherein the drug product comprises a mesenchymal stem cell (MSC) population.

2. The method of claim 1, wherein said step of evaluating at least said properties comprises evaluating all three properties (a), (b) and (c).

3. The method of claim 1, wherein said at least two assays are functional and/or potency assays.

4. The method of claim 3, wherein an individual score value is assigned to the results of each functional and/or potency assay evaluating at least one of properties (a), (b) and/or (c) and wherein said overall assessment comprises allocating a total score value of the in vitro prediction and the total score value is an additive total score value or a weighed total score value.

5. The method of claim 4, wherein the individual score value is assigned based on a comparison of the assay result to at least one reference result or wherein the individual score value is assigned based on a comparison of the assay result to an absolute value.

6. The method of claim 4, wherein in the case of a higher individual score value being indicative of more desirable assay result, a higher total score value is indicative of in vitro prediction of desirable in vivo efficacy; or wherein in the case of a lower individual score value being indicative of more desirable assay result, a lower total score value is indicative of in vitro prediction of desirable in vivo efficacy.

7. The method of claim 1, wherein at least one of said assays measures the immunosuppressive capacity of said drug product by measuring the indoleamine-2,3-dioxygenase (IDO) activity in property b) and/or by measuring prostaglandin E2 secreted by said drug product in property b).

8. The method of claim 1, wherein said at least one of said assays measures the immunosuppressive capacity of said drug product by measuring the effect of said drug product on the proliferation of said patient's own peripheral blood mononuclear cells (PBMCs) in property (a).

9. The method of claim 1, wherein said drug is selected from whole cells, live cells, dead cells, lyophilized cells, extracellular vesicles obtained from cell culture, and exosomes.

10. The method of claim 1, wherein said drug product is live mesenchymal stem cells (MSCs) or isolated live MSCs.

11. The method of claim 1, wherein said drug product is a pooled allogeneic MSC population, such as an isolated pooled allogenic MSC population.

12. The method of claim 1, wherein evaluation of property (a) and/or (b) comprises co-cultivation of the patient's own immune cells with the drug product.

13. The method of claim 1, wherein said evaluating predicts if a therapeutically desirable response will occur in said patient to treatment with said drug product.

14. The method of claim 1, wherein said evaluating predicts if an immunological reaction will occur in said patient to said drug product.

15. The method of claim 1, wherein said patient suffers from a disorder which may be subject to treatment with the drug product, wherein said disorder is selected from the group consisting of autoimmune diabetes, amyotrophic lateral sclerosis and renal transplantation associated complications.

16. The method of claim 15, wherein the disorder is amyotrophic lateral sclerosis.

17. The method of claim 15, wherein the disorder is autoimmune diabetes.

* * * * *